United States Patent
Swanson et al.

(10) Patent No.: US 12,090,327 B2
(45) Date of Patent: Sep. 17, 2024

(54) SYNCHRONIZED PITCH AND TIMING CUES IN A HEARING PROSTHESIS SYSTEM

(71) Applicant: Cochlear Limited, Macquarie University (AU)

(72) Inventors: Brett Anthony Swanson, St. Ives (AU); Zachary Mark Smith, Pymble (AU)

(73) Assignee: Cochlear Limited, Macquarie University (AU)

( * ) Notice: Subject to any disclaimer, the term of this patent is extended or adjusted under 35 U.S.C. 154(b) by 490 days.

(21) Appl. No.: 17/294,138

(22) PCT Filed: Oct. 26, 2020

(86) PCT No.: PCT/IB2020/060024
§ 371 (c)(1),
(2) Date: May 14, 2021

(87) PCT Pub. No.: WO2021/084400
PCT Pub. Date: May 6, 2021

(65) Prior Publication Data
US 2022/0008732 A1   Jan. 13, 2022

Related U.S. Application Data

(60) Provisional application No. 62/927,766, filed on Oct. 30, 2019.

(51) Int. Cl.
H04R 3/00 (2006.01)
A61N 1/36 (2006.01)
H04R 25/00 (2006.01)

(52) U.S. Cl.
CPC ..... *A61N 1/36192* (2013.01); *A61N 1/36038* (2017.08); *A61N 1/36171* (2013.01); *H04R 25/606* (2013.01)

(58) Field of Classification Search
CPC .............. A61N 1/0541; A61N 1/36038; A61N 1/36146; A61N 1/36171; A61N 1/36192;
(Continued)

(56) References Cited

U.S. PATENT DOCUMENTS 7,231,257 B2  6/2007  McDermott et al.
7,310,558 B2  12/2007  Van Hoesel
(Continued)

FOREIGN PATENT DOCUMENTS

CN  102596309 A  7/2012
CN  104685907 A  6/2015
(Continued)

OTHER PUBLICATIONS

Extended European Search Report in counterpart European Application No. 20880382.5, mailed Oct. 13, 2023, 6 pages.
(Continued)

*Primary Examiner* — Gerald Gauthier
(74) *Attorney, Agent, or Firm* — Edell, Shapiro & Finnan, LLC

(57) ABSTRACT

Presented herein are binaural hearing prosthesis systems that are configured to provide a recipient with pitch cues at both ears, while preserving/retaining binaural timing cues.

20 Claims, 11 Drawing Sheets

(58) Field of Classification Search
CPC .................. H04R 25/552; H04R 25/606; H04R 2225/67; H04R 3/00
See application file for complete search history.

(56) References Cited

U.S. PATENT DOCUMENTS

| | | |
|---|---|---|
| 8,503,704 B2 | 8/2013 | Francart et al. |
| 9,084,893 B2 | 7/2015 | Vandali et al. |
| 9,180,295 B2 | 11/2015 | Schleich et al. |
| 9,283,376 B2 | 3/2016 | Wouters et al. |
| 10,226,624 B2 | 3/2019 | Dietz et al. |
| 2005/0107843 A1 | 5/2005 | McDermott et al. |
| 2008/0319509 A1 | 12/2008 | Laback et al. |
| 2009/0030484 A1 | 1/2009 | Chambers |
| 2009/0149916 A1 | 6/2009 | Kwak |
| 2009/0319005 A1 | 12/2009 | Lineaweaver |
| 2012/0004706 A1 | 1/2012 | Meister et al. |
| 2012/0303093 A1* | 11/2012 | Wouters .............. A61N 1/0541 607/57 |
| 2013/0282077 A1* | 10/2013 | Saoji ................ A61N 1/36038 607/57 |
| 2016/0022991 A1* | 1/2016 | Apoux ............... A61N 1/36038 607/57 |
| 2016/0367805 A1 | 12/2016 | Dietz et al. |
| 2018/0193642 A1* | 7/2018 | Chen ..................... H04R 25/552 |
| 2018/0311500 A1 | 11/2018 | Fruhauf et al. |
| 2022/0008732 A1* | 1/2022 | Swanson ............ A61N 1/36192 |
| 2022/0323756 A1* | 10/2022 | Penninger .......... A61N 1/36192 |
| 2022/0355109 A1* | 11/2022 | Brehm ............... A61N 1/36146 |

FOREIGN PATENT DOCUMENTS

| | | |
|---|---|---|
| CN | 109963615 A | 7/2019 |
| EP | 4052486 A1 | 9/2022 |
| WO | 2019-073439 A1 | 4/2019 |
| WO | 2021084400 A1 | 5/2021 |

OTHER PUBLICATIONS

International Search Report and Written Opinion in counterpart International Application No. PCT/IB2020/060024, mailed Feb. 2, 2021, 15 pages.

\* cited by examiner

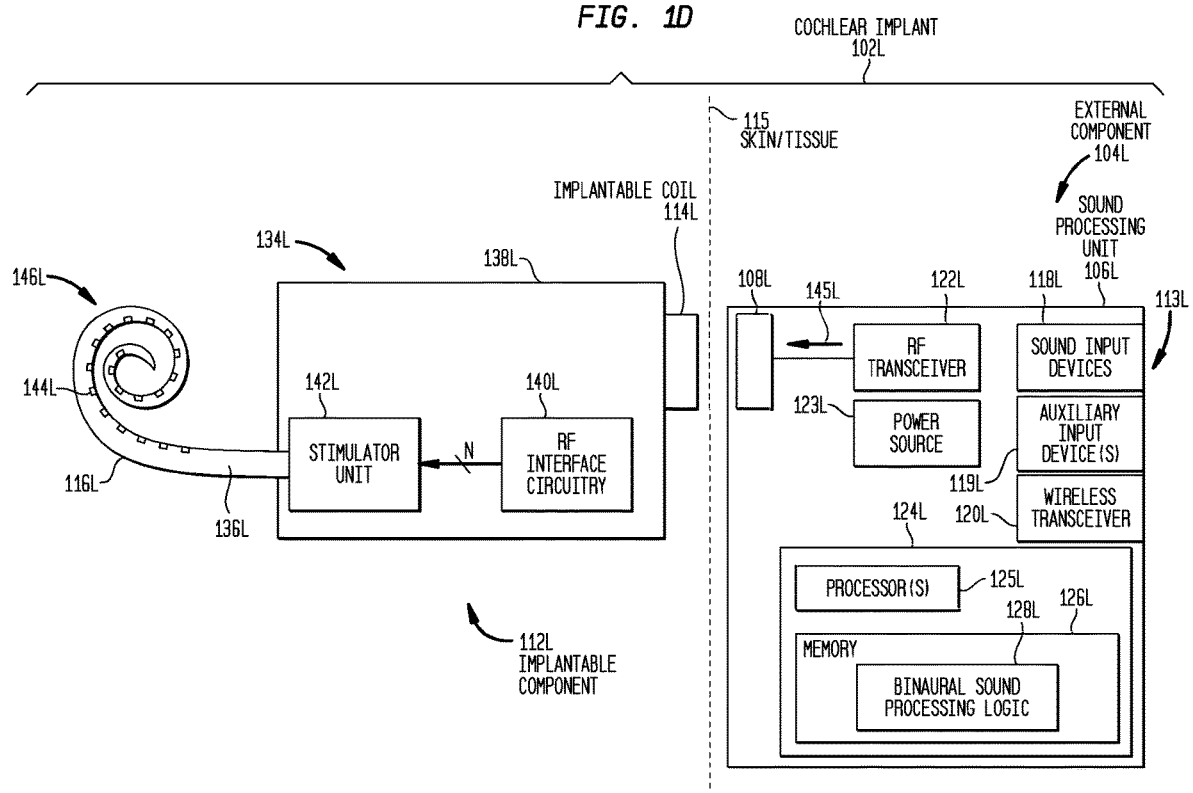

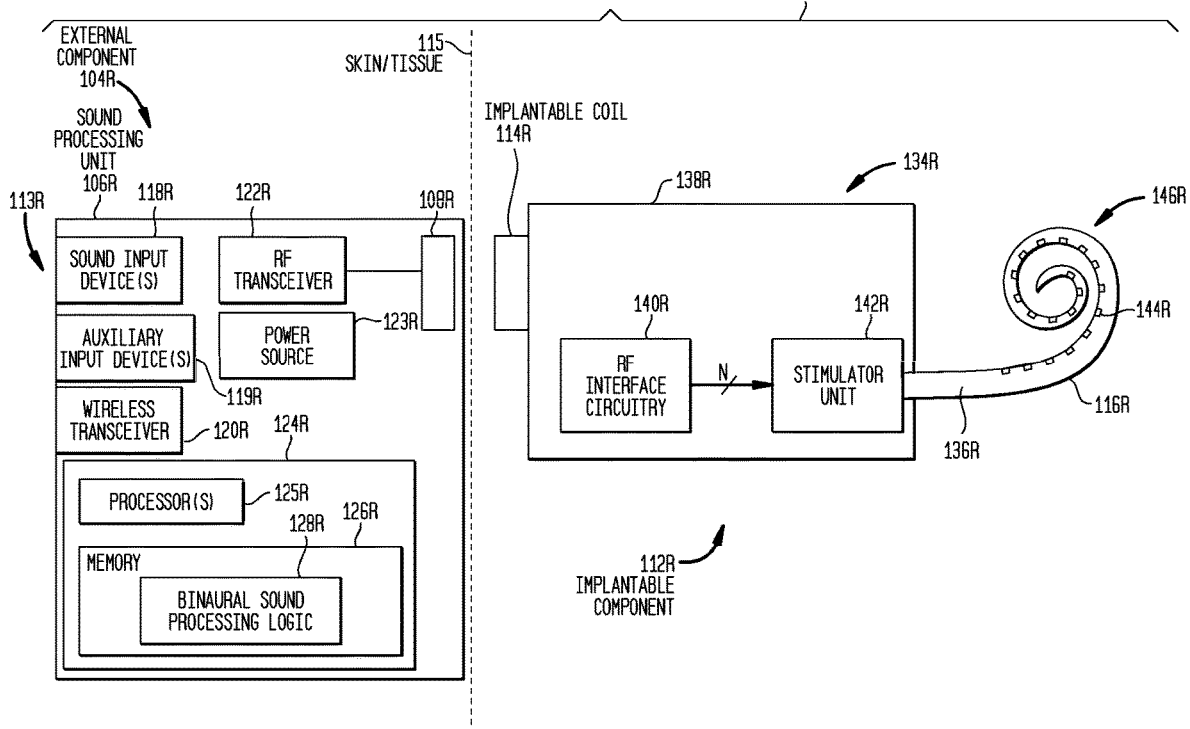

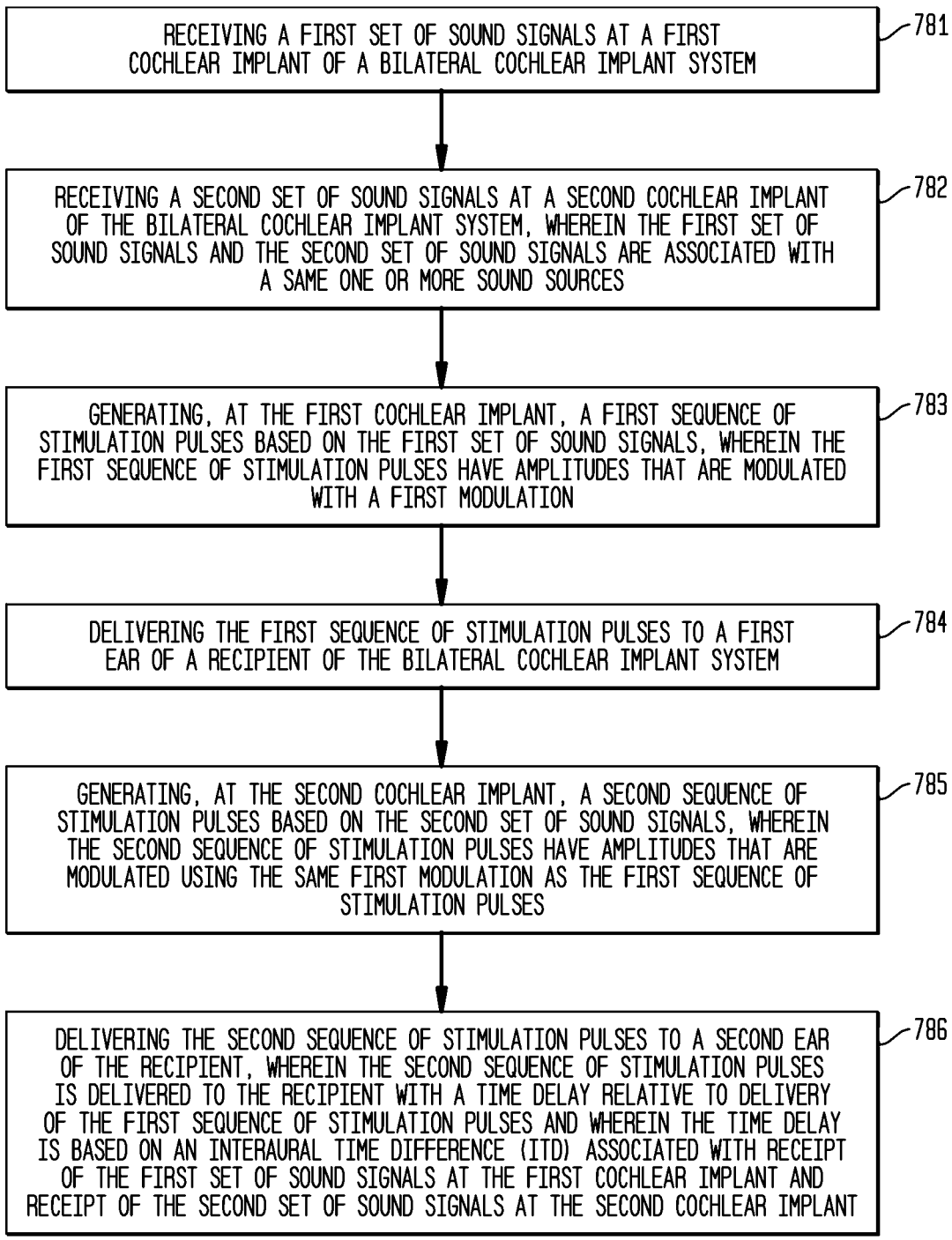

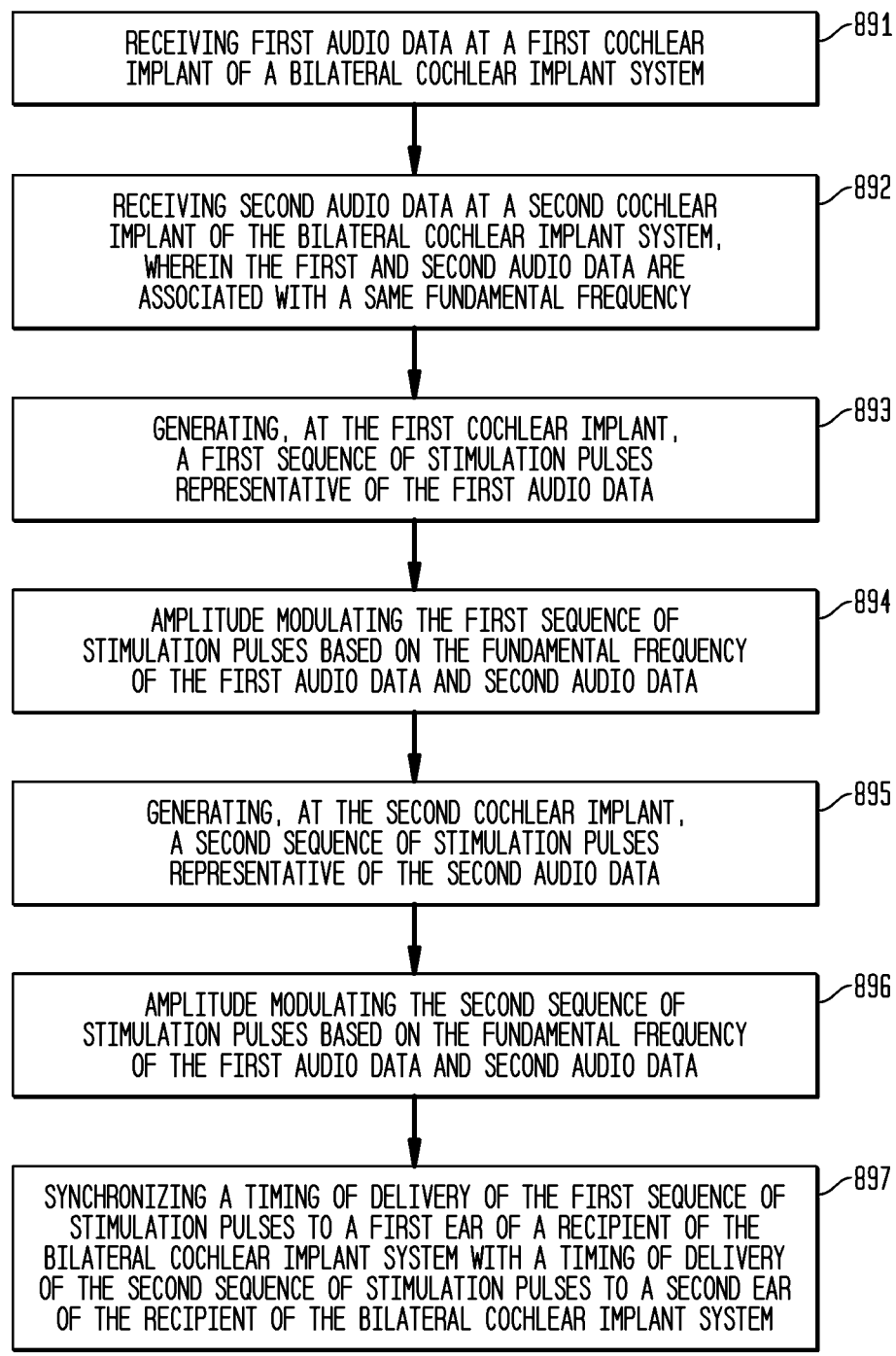

SYNCHRONIZED PITCH AND TIMING CUES IN A HEARING PROSTHESIS SYSTEM

BACKGROUND

Field of the Invention

The present invention relates generally to hearing prosthesis systems.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect presented herein, a method is provided. The method comprises: receiving a first set of sound signals at a first cochlear implant of a bilateral cochlear implant system; receiving a second set of sound signals at a second cochlear implant of the bilateral cochlear implant system, wherein the first set of sound signals and the second set of sound signals are associated with a same one or more sound sources; generating, at the first cochlear implant, a first sequence of stimulation pulses based on the first set of sound signals, wherein the first sequence of stimulation pulses have amplitudes that are modulated with a first modulation; delivering the first sequence of stimulation pulses to a first ear of a recipient of the bilateral cochlear implant system; generating, at the second cochlear implant, a second sequence of stimulation pulses based on the second set of sound signals, wherein the second sequence of stimulation pulses have amplitudes that are modulated using the same first modulation as the first sequence of stimulation pulses; and delivering the second sequence of stimulation pulses to a second ear of the recipient, wherein the second sequence of stimulation pulses is delivered to the recipient with a time delay relative to delivery of the first sequence of stimulation pulses and wherein the time delay is based on an Interaural Time Difference (ITD) associated with receipt of the first set of sound signals at the first cochlear implant and receipt of the second set of sound signals at the second cochlear implant.

In another aspect, a cochlear implant system is provided. The cochlear implant system comprises: a first cochlear implant configured to: receive a first set of sound signals associated with at least one sound source, convert the first set of sound signals into a first stimulation pulse train, wherein the first stimulation pulse train is artificially amplitude modulated based on a fundamental frequency associated with the at least one sound source, and deliver the first stimulation pulse train to a first ear of a recipient of the cochlear implant system; and a second cochlear implant configured to: receive a second set of sound signals associated with the at least one sound source, convert the second set of sound signals into a second stimulation pulse train, wherein the second stimulation pulse train is artificially amplitude modulated based on the fundamental frequency associated with the at least one sound source, and deliver the second stimulation pulse train to a second ear of the recipient with a time delay relative to delivery of the first stimulation pulse train to a first ear of a recipient.

In another aspect, a method is provided. The method comprises: receiving a first set of sound signals at a first cochlear implant of a bilateral cochlear implant system; receiving a second set of sound signals at a second cochlear implant of the bilateral cochlear implant system, wherein the first set of sound signals and the second set of sound signals are associated with a same one or more sound sources; generating, at the first cochlear implant, a first sequence of stimulation pulses based on the first set of sound signals, wherein the first sequence of stimulation pulses have amplitudes that are modulated with a first modulation; delivering the first sequence of stimulation pulses to a first ear of a recipient of the bilateral cochlear implant system; generating, at the second cochlear implant, a second sequence of stimulation pulses based on the second set of sound signals, wherein the second sequence of stimulation pulses have amplitudes that are modulated using the same first modulation as the first sequence of stimulation pulses; and delivering the second sequence of stimulation pulses to a second ear of the recipient, wherein the second sequence of stimulation pulses is delivered to the recipient with a time delay relative to delivery of the first sequence of stimulation pulses and wherein the time delay is based on an Interaural Time Difference (ITD) associated with receipt of the first set of sound signals at the first cochlear implant and receipt of the second set of sound signals at the second cochlear implant.

In another aspect, a cochlear implant system is provided. The cochlear implant system comprises: a first cochlear implant configured to: receive a first set of sound signals generated by at least one sound source, convert the first set of sound signals into a first stimulation pulse train, wherein the first stimulation pulse train is artificially amplitude modulated based on a fundamental frequency associated with the at least one sound source, and deliver the first stimulation pulse train to a first ear of a recipient of the cochlear implant system; and a second cochlear implant configured to: receive a second set of sound signals generated by the at least one sound source, convert the second set of sound signals into a second stimulation pulse train, wherein the second stimulation pulse train is artificially amplitude modulated based on the fundamental frequency associated with the at least one sound source, determine, relative to delivery of the first stimulation pulse train to the first ear of the recipient, a time delay for delivery of the second stimulation pulse train to a second ear of the recipient, and deliver the second stimulation pulse train to the second ear of the recipient at a time corresponding to the time delay.

In another aspect, non-transitory computer readable storage media encoded with instructions are provided. The instructions, when executed by one or more processors, cause the one or more processors to: generate, at a first cochlear implant of a cochlear implant system, a first sequence of stimulation pulses representative of first audio data received at the first cochlear implant; modulate the first sequence of stimulation pulses based on one or more features of the first audio data and the second audio data; generate, at a second cochlear implant of the cochlear implant system, a second sequence of stimulation pulses representative of second audio data received at the second cochlear implant; and modulate the second sequence of stimulation pulses based on the one or more features of the first audio data and the second audio data.

BRIEF DESCRIPTION OF THE DRAWINGS

Embodiments of the present invention are described herein in conjunction with the accompanying drawings, in which:

FIGS. 1D and 1E are block diagrams of sound processing units forming part of the cochlear implant system of FIG. 1A;

FIG. 7 is a flowchart of a method, in accordance with certain embodiments presented herein; and FIG. 8 is a flowchart of another method, in accordance with certain embodiments presented herein.

DETAILED DESCRIPTION

Figure 1A:
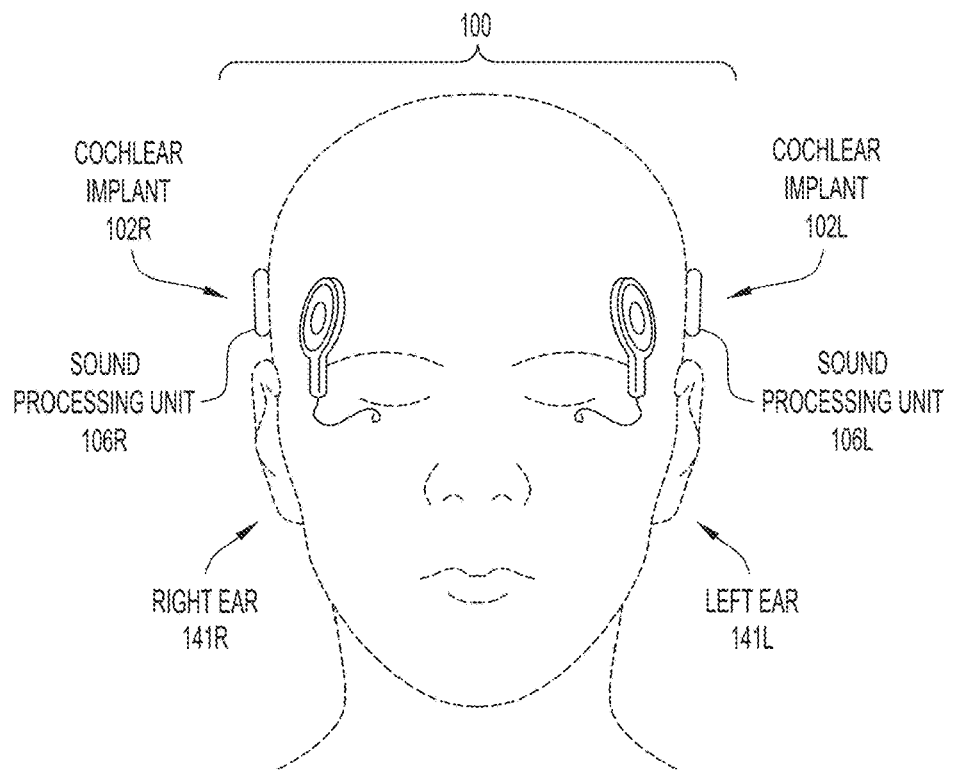
FIG. 1A is a schematic view of a cochlear implant system in which embodiments presented herein may be implemented.

Medical devices and medical device systems (e.g., including multiple implantable medical devices) have provided a wide range of therapeutic benefits to recipients over recent decades. For example, a hearing prosthesis system is a type of implantable medical device system that includes one or more hearing prostheses that operate to convert sound signals into one or more acoustic, mechanical, and/or electrical stimulation signals for delivery to a recipient. The one or more hearing prostheses that can form part of a hearing prosthesis system include, for example, hearing aids, cochlear implants, middle ear stimulators, bone conduction devices, brain stem implants, electro-acoustic cochlear implants or electro-acoustic devices, and other devices providing acoustic, mechanical, and/or electrical stimulation to a recipient.

One specific type of hearing prosthesis system, referred to herein as a "binaural hearing prosthesis system" or more simply as a "binaural system," includes two hearing prostheses, where one of the two hearing prosthesis is positioned at each ear of the recipient. More specifically, in a binaural system each of the two prostheses provides stimulation to one of the two ears of the recipient (i.e., either the right or the left ear of the recipient).

Presented herein are binaural hearing prosthesis systems, such as binaural or bilateral cochlear implant systems, that are configured to provide a recipient with pitch cues at both ears, while preserving/retaining binaural timing cues. More specifically, a binaural or bilateral cochlear implant system comprises first and second cochlear implants positioned at first and second ears, respectively, of a recipient. The first cochlear implant is configured to capture/receive a first set of sound signals and convert the first set of sound signals into a first stimulation pulse sequence for delivery to the first ear of the recipient. Similarly, the second cochlear implant is configured to receive a second set of sound signals and convert the second set of sound signals into a second stimulation pulse sequence for delivery to the second ear of the recipient. Each of the first and second stimulation pulse sequences are amplitude modulated based on the fundamental frequency (F0) of the first and second sets sound signals, which are associated with a same one or more sound sources, thereby providing the recipient with a pitch cue.

Additionally, the first and second sets of sound signals will be received at the first and second cochlear implants with a relative timing that corresponds to a relative location of the one or more sound sources. The first and second cochlear implants are configured to synchronize delivery of the first sequence of stimulation pulses to a first ear of the recipient with delivery of the second sequence of stimulation pulses to a second ear of the recipient based on the relative timing, thereby providing the recipient with a binaural timing cue.

It is to be appreciated that the techniques presented herein may implemented with any of a number of medical devices and systems, including in conjunction with cochlear implants or other auditory prostheses, balance prostheses (e.g., vestibular implants), retinal or other visual prostheses, cardiac devices (e.g., implantable pacemakers, defibrillators, etc.), seizure devices, sleep apnea devices, electroporation devices, spinal cord stimulators, deep brain stimulators, motor cortex stimulators, sacral nerve stimulators, pudendal nerve stimulators, vagus/vagal nerve stimulators, trigeminal nerve stimulators, diaphragm (phrenic) pacers, pain relief stimulators, other neural, neuromuscular, or functional stimulators, etc. However, merely for ease of description, aspects of the techniques will be generally described with reference to a specific medical device system, namely a bilateral cochlear implant systems. As used herein, a "bilateral" cochlear implant system is a system that includes first and second cochlear implants located at first and second ears, respectively, of a recipient. In such systems, each of the two cochlear implant system delivers stimulation (current)

pulses to one of the two ears of the recipient (i.e., either the right or the left ear of the recipient). In a bilateral cochlear implant system, one or more of the two cochlear implants may also deliver acoustic stimulation to the ears of the recipient (e.g., an electro-acoustic cochlear implant) and/or the two cochlear implants need not be identical with respect to, for example, the number of electrodes used to electrically stimulate the cochlea, the type of stimulation delivered, etc.

Figure 1B:
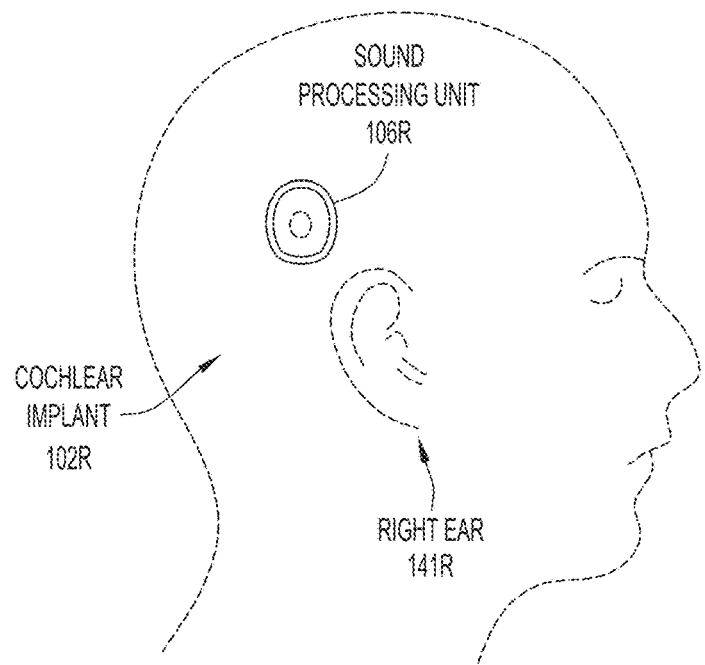
FIG. 1B is a side view of a recipient wearing the cochlear implant system of FIG. 1A.
Figure 1C:
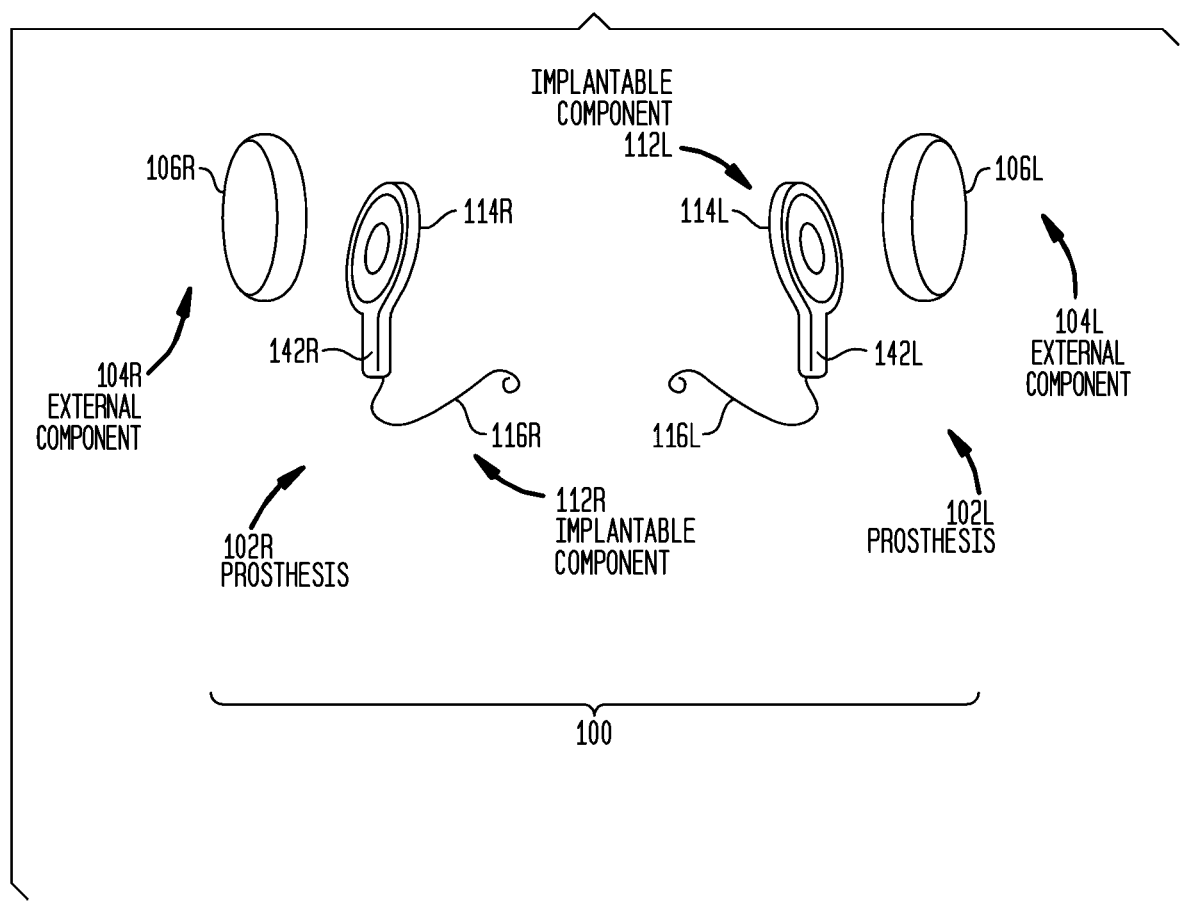
FIG. 1C is a schematic view of the components of the cochlear implant system of FIG. 1A.

FIGS. 1A-1E are diagrams illustrating one example bilateral cochlear implant system 100 configured to implement the techniques presented herein. More specifically, FIGS. 1A-1E illustrate an example bilateral system 100 comprising left and right cochlear implants, referred to as cochlear implant 102L and cochlear implant 102R. FIGS. 1A and 1B are schematic drawings of a recipient wearing the left cochlear implant 102L at a left ear 141L and the right cochlear implant 102R at a right ear 141R, while FIG. 1C is a schematic view of each of the left and right cochlear implants. FIGS. 1D and 1E are block diagrams illustrating further details of the left cochlear implant 102L and the right cochlear implant 102R, respectively.

Referring specifically to FIG. 1C, cochlear implant 102L includes an external component 104L that is configured to be directly or indirectly attached to the body of the recipient and an implantable component 112L configured to be implanted in the recipient. The external component 104L comprises a sound processing unit 106L, while the implantable component 112L includes an internal coil 114L, a stimulator unit 142L and an elongate stimulating assembly (electrode array) 116L implanted in the recipient's left cochlea (not shown in FIG. 1C).

The cochlear implant 102R is substantially similar to cochlear implant 102L. In particular, cochlear implant 102R includes an external component 104R comprising a sound processing unit 106R, and an implantable component 112R comprising internal coil 114R, stimulator unit 142R, and elongate stimulating assembly 116R.

FIG. 1D is a block diagram illustrating further details of cochlear implant 102L, while FIG. 1E is a block diagram illustrating further details of cochlear implant 102R. As noted, cochlear implant 102R is substantially similar to cochlear implant 102L and includes like elements as that described below with reference to cochlear implant 102L. For ease of description, further details of cochlear implant 102R have been omitted from the description.

As noted, the external component 104L of cochlear implant 102L includes a sound processing unit 106L. The sound processing unit 106L comprises one or more input devices 113L that are configured to receive input signals (e.g., sound or data signals). In the example of FIG. 1D, the one or more input devices 113L include one or more sound input devices 118L (e.g., microphones, audio input ports, telecoils, etc.), one or more auxiliary input devices 119L (e.g., audio ports, such as a Direct Audio Input (DAI), data ports, such as a Universal Serial Bus (USB) port, cable port, etc.), and a wireless transmitter/receiver (transceiver) 120L. However, it is to be appreciated that one or more input devices 113L may include additional types of input devices and/or less input devices (e.g., the wireless transceiver 120L and/or one or more auxiliary input devices 119L could be omitted).

The sound processing unit 106L also comprises one type of a closely-coupled transmitter/receiver (transceiver) 122L, referred to as or radio-frequency (RF) transceiver 122L, a power source 123L, and a processing module 124L. The processing module 124L comprises one or more processors 125L and a memory 126L that includes binaural sound processing logic 128L. In the examples of FIGS. 1A-1E, the sound processing unit 106L and the sound processing unit 106R are off-the-ear (OTE) sound processing units (i.e., components having a generally cylindrical shape and which is configured to be magnetically coupled to the recipient's head), etc. However, it is to be appreciated that embodiments of the present invention may be implemented by sound processing units having other arrangements, such as by a behind-the-ear (BTE) sound processing unit configured to be attached to and worn adjacent to the recipient's ear, including a mini or micro-BTE unit, an in-the-canal unit that is configured to be located in the recipient's ear canal, a body-worn sound processing unit, etc.

The implantable component 112L comprises an implant body (main module) 134L, a lead region 136L, and the intra-cochlear stimulating assembly 116L, all configured to be implanted under the skin/tissue (tissue) 115 of the recipient. The implant body 134L generally comprises a hermetically-sealed housing 138L in which RF interface circuitry 140L and a stimulator unit 142L are disposed. The implant body 134L also includes the internal/implantable coil 114L that is generally external to the housing 138L, but which is connected to the transceiver 140L via a hermetic feedthrough (not shown in FIG. 1D).

As noted, stimulating assembly 116L is configured to be at least partially implanted in the recipient's cochlea. Stimulating assembly 116L includes a plurality of longitudinally spaced intra-cochlear electrical stimulating contacts (electrodes) 144L that collectively form a contact or electrode array 146L for delivery of electrical stimulation (current) to the recipient's cochlea.

Stimulating assembly 116L extends through an opening in the recipient's cochlea (e.g., cochleostomy, the round window, etc.) and has a proximal end connected to stimulator unit 142L via lead region 136L and a hermetic feedthrough (not shown in FIG. 1D). Lead region 136L includes a plurality of conductors (wires) that electrically couple the electrodes 144L to the stimulator unit 142L.

As noted, the cochlear implant 102L includes the external coil 108L and the implantable coil 114L. The coils 108L and 114L are typically wire antenna coils each comprised of multiple turns of electrically insulated single-strand or multi-strand platinum or gold wire. Generally, a magnet is fixed relative to each of the external coil 108L and the implantable coil 114L. The magnets fixed relative to the external coil 108L and the implantable coil 114L facilitate the operational alignment of the external coil 108L with the implantable coil 114L. This operational alignment of the coils enables the external component 104L to transmit data, as well as possibly power, to the implantable component 112L via a closely-coupled wireless link formed between the external coil 108L with the implantable coil 114L. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 206L includes the processing module 124L. The processing module 124L is configured to convert received input signals (received at one or more of the input devices 113L) into output signals 145L for use in stimulating a first ear of a recipient (i.e., the processing module 124L is configured to perform sound processing on input signals received at the sound processing unit 106L). Stated differently, in the sound processing mode, the one or more processors 125L are configured to execute binaural sound processing logic 128L in memory 126L to convert the received input signals into output signals 145L that represent electrical stimulation for delivery to the recipient.

In the embodiment of FIG. 1D, the output signals 145L are provided to the RF transceiver 114, which transcutaneously transfers the output signals 145L (e.g., in an encoded manner) to the implantable component 112L via external coil 108L and implantable coil 114L. That is, the output signals 145L are received at the RF interface circuitry 140L via implantable coil 114L and provided to the stimulator unit 142L. The stimulator unit 142L is configured to utilize the output signals 145L to generate electrical stimulation signals (e.g., current signals) for delivery to the recipient's cochlea via one or more stimulating contacts 144L. In this way, cochlear implant 102L electrically stimulates the recipient's auditory nerve cells, bypassing absent or defective hair cells that normally transduce acoustic vibrations into neural activity, in a manner that causes the recipient to perceive one or more components of the received sound signals.

As noted, cochlear implant 102R is substantially similar to cochlear implant 102L and comprises external component 104R and implantable component 112R. External component 104R includes a sound processing unit 106R that comprises external coil 108R, input devices 113R (i.e., one or more sound input devices 118R, one or more auxiliary input devices 119R, and wireless transceiver 120R), closely-coupled transceiver (RF transceiver) 122R, power source 123R, and processing module 124R. The processing module 124R includes one or more processors 125R and a memory 126R that includes binaural sound processing logic 128R. The implantable component 112R includes an implant body (main module) 134R, a lead region 136R, and the intra-cochlear stimulating assembly 116R, all configured to be implanted under the skin/tissue (tissue) 115 of the recipient. The implant body 134R generally comprises a hermetically-sealed housing 138R in which RF interface circuitry 140L and a stimulator unit 142R are disposed. The implant body 134R also includes the internal/implantable coil 114R that is generally external to the housing 138R, but which is connected to the RF interface circuitry 140R via a hermetic feedthrough (not shown in FIG. 1E). The stimulating assembly 116R includes a plurality of longitudinally spaced intra-cochlear electrical stimulating contacts (electrodes) 144R that collectively form a contact or electrode array 146R for delivery of electrical stimulation (current) to the recipient's cochlea. Each of the elements of cochlear implant 102R shown in FIG. 1E are similar to like-numbered elements of cochlear implant 102L shown in FIG. 1D.

In normal hearing, the main binaural cues for left/right sound localization are the Interaural (Inter-aural) Level Difference (ILD) and the Interaural (Inter-aural) Time Difference (ITD). A primary benefit of a bilateral cochlear implant system is that such systems can provide a recipient with ILD (inter-aural level difference) cues. However, existing bilateral cochlear implant systems do not provide recipients with correct ITD cues.

Presented herein are techniques that enable a bilateral cochlear implant system to provide a recipient with pitch cues (stimulation pulse sequence amplitude modulation) in a manner that does not disturb the ITD cues (i.e., enable a recipient to benefit from both pitch cues and binaural timing cues). More specifically, in the example of FIGS. 1A-1E, the cochlear implant 102L is configured to receive first set of sound signals and convert the first set of sound signals into a first stimulation pulse sequence for delivery to the first ear of the recipient. Similarly, the cochlear implant 102R is configured to receive a second set of sound signals and convert the second set of sound signals into a second stimulation pulse sequence for delivery to the second ear of the recipient. The first and second stimulation pulse sequences generated by cochlear implants 102L and 102R, respectively, are amplitude modulated based on the fundamental frequency (F0) of the first and second sets sound signals (which are associated with a same one or more sound sources). That is, the modulation of the stimulation pulse amplitudes in the first and second pulse sequences is synchronized across both the left and right sides, and is based on the fundamental frequency of received sound signals Additionally, the first and second sets of sound signals will be received at the cochlear implants 102L and 102R with a relative timing that corresponds to a relative location of the one or more sound sources. That is, cochlear implants 102L and 102R are configured to synchronize delivery of the first sequence of stimulation pulses to a first ear of the recipient with delivery of the second sequence of stimulation pulses to a second ear of the recipient based on the relative location of the sound sources that generated the first and second sets of sound signals. As a result, bilateral cochlear implant system 100 is configured to both improve pitch perception and provide appropriate ITD cues.

Figure 2:
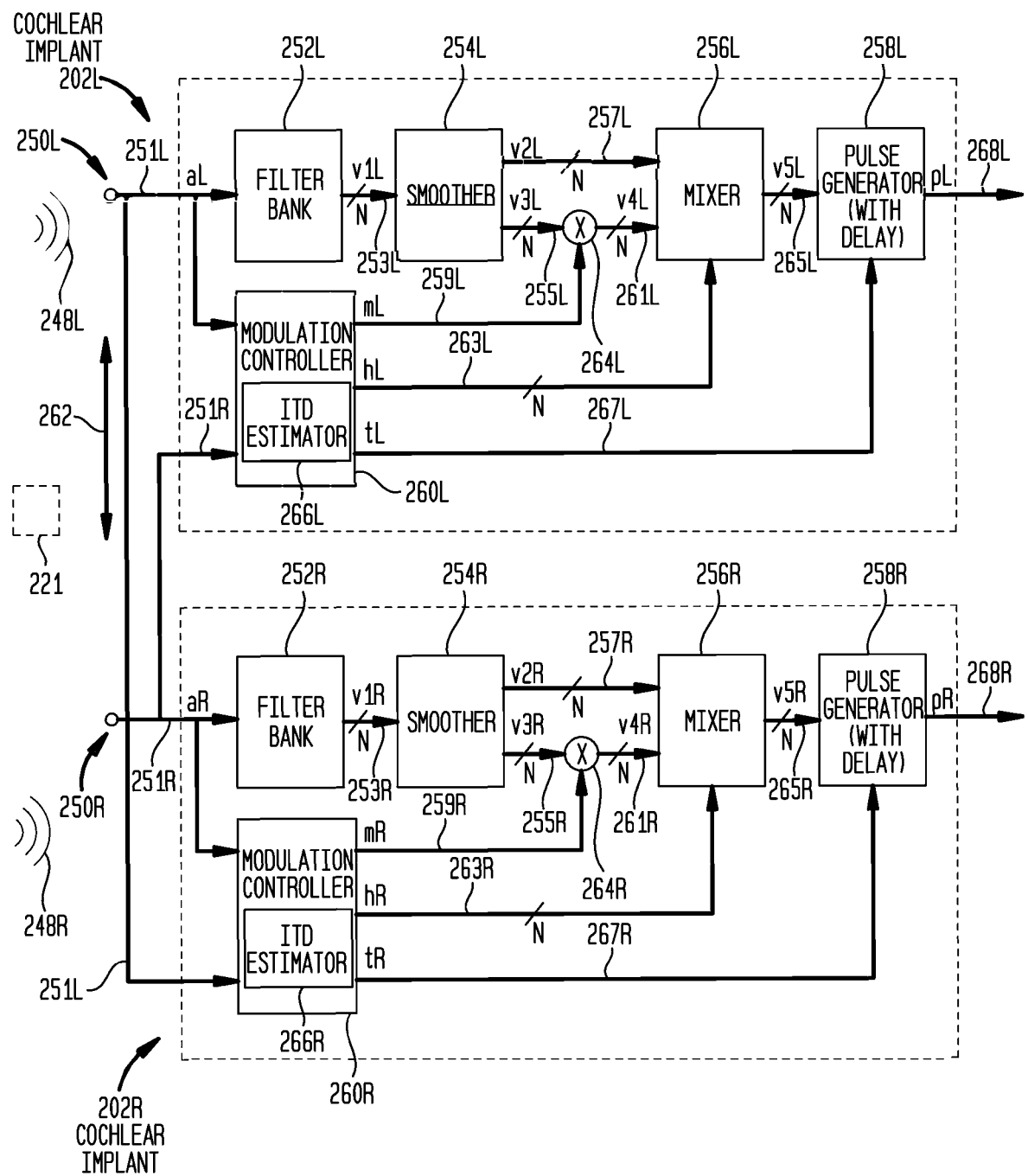
FIG. 2 is a functional block diagram of a cochlear implant system, in accordance with certain embodiments presented herein.

FIG. 2 is a functional block diagram of a bilateral cochlear implant system 200 in accordance with embodiments presented herein. As shown, the bilateral cochlear implant system 200 comprises a left (first) cochlear implant 202L and a right (second) cochlear implant 202R. Referring first to cochlear implant 202L, the cochlear implant comprises a microphone array 250L (e.g., dual-microphone system), a filterbank 252L, a smoother 254L, a mixer 256L, a pulse generator 258L, and a modulation controller 260L.

In certain examples, the operations described below with reference to filterbank 252L, smoother 254L, mixer 256L, and modulation controller 260L may be performed at a processing module, such as processing module 124L of FIG. 1D. Additionally, in certain examples, certain operations described below with reference to pulse generator 258L may be performed at a processing module (e.g., processing module 124L), while other operations may be performed at a stimulator unit, such as stimulator unit 142L of FIG. 1D.

Cochlear implant 202R, which is substantially similar to cochlear implant 202L, comprises a microphone array 250R, a filterbank 252R, a smoother 254R, a mixer 256R, a pulse generator 258R, and a modulation controller 260R. In certain examples, the operations described below with reference to filterbank 252R, smoother 254R, mixer 256R, and modulation controller 260R may be performed at a processing module, such as processing module 124R of FIG. 1E. Additionally, in certain examples, certain operations described below with reference to pulse generator 258R may be performed at a processing module (e.g., processing module 124R), while other operations may be performed at a stimulator unit, such as stimulator unit 142R of FIG. 1E.

Although FIG. 2 will be described with reference to the use of microphone arrays 250L and 250R, it is to be appreciated that the cochlear implants 202L and 202R may also or alternatively include different types and combinations of sound input devices. It is also to be appreciated that the functional blocks shown in FIG. 2 for each of cochlear implants 202L and 202 may be distributed across one, two, or more different physical devices. For example, certain functional blocks shown in FIG. 2 for cochlear implant 202L may be part of an external component (e.g., external component 104L), while other functional blocks for cochlear implant 202L may be part of an implantable component (e.g., implantable component 112L). Alternatively, all of the functional blocks for cochlear implant 202L may be part of an implantable component, the functional blocks for cochlear implant 202L may be split between two external components and an implantable component, etc.

Returning to the example of FIG. 2, a first set of acoustic sound signals (sounds) 248L are received at the microphone array 250L and are used to generate audio data (aL) 251L. More specifically, the audio data 251L is derived from microphone signals, processed by analog-to-digital converters (ADC), a beamformer, and an Automatic Gain Control (AGC), all of which have been omitted from FIG. 2 for ease of illustration. In a similar manner, microphone array 250R converts a second set of acoustic sound signals (sounds) 248R are into audio data (aR) 251R.

Due to the tonotopic mapping of a recipient's cochlea, different portions of the received sound signals 248L and 248R are delivered to different target locations/places in the cochlear via different "stimulation channels." As used herein, a stimulation channel is a combination/set of implanted electrodes that are used simultaneously/collectively to deliver current signals to the cochlea so as to elicit stimulation at a specific target location/place of the cochlea. Due, in part, to the use of different stimulation channels to deliver stimulation to the recipient, the audio data 251L and 251R is applied to the filterbanks 252L and 252R, respectively. The filterbanks 252L and 252R each comprise a band-pass filter and an envelope detector for each of a plurality of stimulation channels. As such, the filterbank 252L produces a set (e.g., a plurality) of filterbank envelopes 253L (v1L) and filterbank 252R produces a set of filterbank envelopes 253R (v1R), where each filterbank envelope is associated with a stimulation channel.

In FIG. 2, the lines/arrows marked by "/N," such as arrows 253L and 253R, indicate sets of related signals, with one signal for each of a plurality of stimulation channels in the cochlear implant system. A typical cochlear implant system may have between 12 and 22 stimulation channels, although other numbers of channels may be used in different embodiments.

The filterbank envelopes 253L and 253R are applied to the smoothers 254L and 254R, respectively, which smooth each of the filterbank envelopes to remove amplitude fluctuations having frequencies within and above an expected range of fundamental frequencies (e.g., 70 Hertz (Hz) and higher). The smoothers 254L and 254R produce a set of smoothed envelope signals 255L (v3L) and 255R (v3R), respectively.

Additionally, the smoothers 254L and 254R delay the sets of filterbank envelopes 253L and 253R, respectively, to produce a set of delayed filterbank envelopes 257L (v2L) and 257R (v2R), respectively, each with a delay that matches the inherent delay that is introduced by the smoothing operation of smoothers 254L and 254R, respectively. In other words, envelopes 255L and 257L are aligned in time and the envelopes 255R and 257R are aligned in time.

As noted elsewhere herein, the first set of acoustic sound signals 248L and the second set of acoustic sound signals 248R are generated by the same one or more sound sources 221. As such, the set of acoustic sound signals 248L and the second set of acoustic sound signals 248R are received "contemporaneously" (i.e., around the same time) by the cochlear implants 202L and 202R. However, the first set of acoustic sound signals 248L and the second set of acoustic sound signals 248R are received at the respective cochlear implants 202L and 202R with a relative timing that corresponds to the location of the one or more sound sources 221. In other words, one of either the first or second set of acoustic sound signals may be received with a delay, relative to the receipt of the other of first or second set of acoustic sound signals. The delay corresponds to the Interaural Time Difference (ITD) between the left and right ears of the recipient, relative to the location of the one or more sound sources. The ITD may change (increase or decrease) as the location of the one or more sound sources 211 changes.

In the example of FIG. 2, cochlear implants 202L and 202R are configured to operate a two-way audio link/channel 262 that enables the transfer of, for example, audio data 251L and 251R between the cochlear implants. That is, the two-way audio channel 262 enables the cochlear implant 202R to send audio data 251R (i.e., send data representing the second set of sound signals 248R) to cochlear implant 202L and, similarly, enables cochlear implant 202L to send audio data 251L (e., send data representing the first set of sound signals 248L) to cochlear implant 202R. Therefore, cochlear implants 202L and 202R each have access to both of the audio data 251L and 251R and, accordingly, both sets of sound signals 248L and 248R. The two-way audio channel 262 may be a wired electrical channel or a wireless channel (e.g., a standardized wireless channel, such as Bluetooth®, Bluetooth® Low Energy (BLE) or other channel interface making use of any number of standard wireless streaming protocols; a proprietary protocol for wireless streaming of the audio data; etc. Bluetooth® is a registered trademark owned by the Bluetooth® SIG).

In the example of FIG. 2, the audio data 251L and the audio data 251R (either received directly or received via the two-way audio channel 262) are applied to both of the modulation controllers 260L and 260R. In general, the modulation controllers 260L and 260R are configured to generate a modulator signal 259L (mL) and 259R (mR), respectively, that each have a period corresponding to the fundamental frequency (F0) of the most dominant harmonic component in the audio data 251L and 251R. That is, the modulation controllers 260L and 260R are each configured to identify the fundamental frequency (F0) associated with received sound signals 248L and 248R. The modulation controllers 260L and 260R then generate the modulation signals 259L and 259R based on the identified fundamental frequency (F0).

In the example of FIG. 2, the modulation controllers 260L and 260R operate on both the ipsilateral (same side) audio data 251L and the contralateral (other side) audio data 251R. In certain embodiments, modulation controller 260L is configured to generate a first estimate of the fundamental frequency, referred to as "$F0_{iL}$," using the ipsilateral audio data 251L and a second estimate of the fundamental frequency, referred to as "$F0_{cL}$" using the contralateral audio 251R. If the two estimates $F0_{iL}$ and $F0_{cL}$ are approximately equal, then it is assumed that there is one dominant sound source in the environment, and binaural processing functions in accordance with embodiments presented are enabled. Conversely, if the two estimates $F0_{iL}$ and $F0_{cL}$ are significantly different, then it is assumed that there is not a single dominant sound source, and the binaural processing functions in accordance with embodiments presented herein may be disabled. The modulation controller 260R may operate in a similar to manner to generate and compare two estimates of the fundamental frequency, referred to as "$F0_{iR}$" (made using the ipsilateral audio data 251R) and $F0_{cR}$" (made using the contralateral audio 251L).

The binaural processing functions in accordance with embodiments presented herein may be disabled when, for example, there is one speaker close to the left ear, and a different speaker close to the right ear. In another example, the binaural processing functions in accordance with embodiments presented herein may be disabled when the recipient is holding a telephone to one ear, while the other ear is exposed to ambient sounds. In this case, the binaural processing functions are disabled so that the cochlear implants 202L and 202R operate independently.

When not disabled, several binaural processing functions in accordance with embodiments presented herein may be applied by the cochlear implant 202L and cochlear implant 202R. Referring first to cochlear implant 202L, a first binaural processing function in accordance with embodiments presented herein is that the two F0 estimates $F0_{iL}$ and $F0_{cL}$ are combined into a single joint estimate, referred to as "$F0_{jL}$." This joint estimate $F0_{jL}$ is then used to generate the modulation signal 259L. At 264L, the modulation signal 259L is used to modulate the smoothed envelope signals 255L, producing modulated envelope signals 261L (v4L).

Cochlear implant 202R operates in a similar manner to combine the two F0 estimates $F0_{iR}$ and $F0_{cR}$ into a single joint estimate, referred to as "$F0_{jR}$," which is then used to generate the modulation signal 259R. The modulation signal 259R is used to modulate the smoothed envelope signals 255R, producing modulated envelope signals 261R (v4R).

In addition to generating modulator signals 259L and 259R, the modulation controllers 260L and 260R are each configured to generate an estimate, for each of the plurality of band-pass filter channels, of the probability that the signal component in the corresponding band-pass filter channel is harmonically related to the dominant harmonic component in the audio data 251L and 251R. As such, the modulation controller 260L generates a set 263L of harmonic probability signals (hL) and modulation controller 260R generates a set 263R of harmonic probability signals (hR). Each signal in the sets 263L and 263R corresponds to one of the band-pass filter channels and provides an estimate of the probability that the signal in that corresponding band-pass filter channel is harmonically related to the dominant harmonic component in audio data 251L and 251R.

The sets 263L and 263R of harmonic probability signals are applied to the mixers 256L and 256R, respectively. The mixer 256L is configured to sum the delayed filterbank envelopes 257L (v2L) and the modulated envelope signals 261L (v4L), with the relative proportions of each controlled by the harmonic probability signals in set 261L. The mixer 256L produces a set 265L of modulated output envelopes (v5L). The set 265L of modulated output envelopes are then applied to the pulse generator 258L. Mixer 256R operates in a similar manner to sum the delayed filterbank envelopes 257R (v2R) and the modulated envelope signals 261R (v4R), with the relative proportions of each controlled by the harmonic probability signals in set 261R. The mixer 256R produces a set 265R of modulated output envelopes (v5R). The set 265R of modulated output envelopes are then applied to the pulse generator 258R.

A second binaural processing function at cochlear implants 202L and 202E is implemented by an Interaural Time Difference (ITD) estimators 266L and 266R of the modulation controllers 260L and 260R, respectively, which determine the ITD of the most dominant harmonic component in audio data 251L and 251R. The ITD estimate generated by the ITD estimator 266L controls the delay signal 267L (tL), while the ITD estimate generated by the ITD estimator 266R controls the delay signal 267R (tR). More specifically, if the most dominant harmonic sound source is on the left side of the recipient's head (i.e., proximate to cochlear implant 202L), then the delay signal 267L will be zero, and delay signal 267R will represent the time delay required for the sounds from the most dominant harmonic sound source to reach the right ear. However, if the dominant harmonic sound source is on the right side of the recipient's head (i.e., proximate to cochlear implant 202R), then the delay signal 267R will be zero, and the delay signal 267L will represent the time delay required for the sounds from the most dominant harmonic sound source to reach the left ear. If the dominant harmonic sound source is directly in front of the recipient, then both delay signals 267L and 267R will be zero, as there is no ITD between the left and right ears for a sound source directly in front of the recipient. If the binaural processing functions are disabled, then no ITD estimate is made and delay signals 267L and 267R will also be zero.

Delay signals 267L and 267R are applied to the pulse generators 258L and 258R, respectively. As noted above, the set 265L of output envelopes (v5L) are also applied to the pulse generator 258L, while the set 265R of output envelopes (v5R) are also applied to the pulse generator 258R. The pulse generator 258L is configured to sample the set 265L of output envelopes (v5L) to produce a stimulation pulse sequence 268L (i.e., a sequence of stimulation pulses (pL)). Similarly, pulse generator 258R is configured to sample the set 265R of output envelopes (v5R) to produce a stimulation pulse sequence 268R (pL). In the example of FIG. 2, the pulses with one of the stimulation pulse sequences 268L or 268R are delayed by a time interval controlled by the delay signals 267L or 267R, (i.e., the pulses are generated with a time delay that is based on the ITD estimate made by modulation controllers 260L and 260R).

Figure 3:
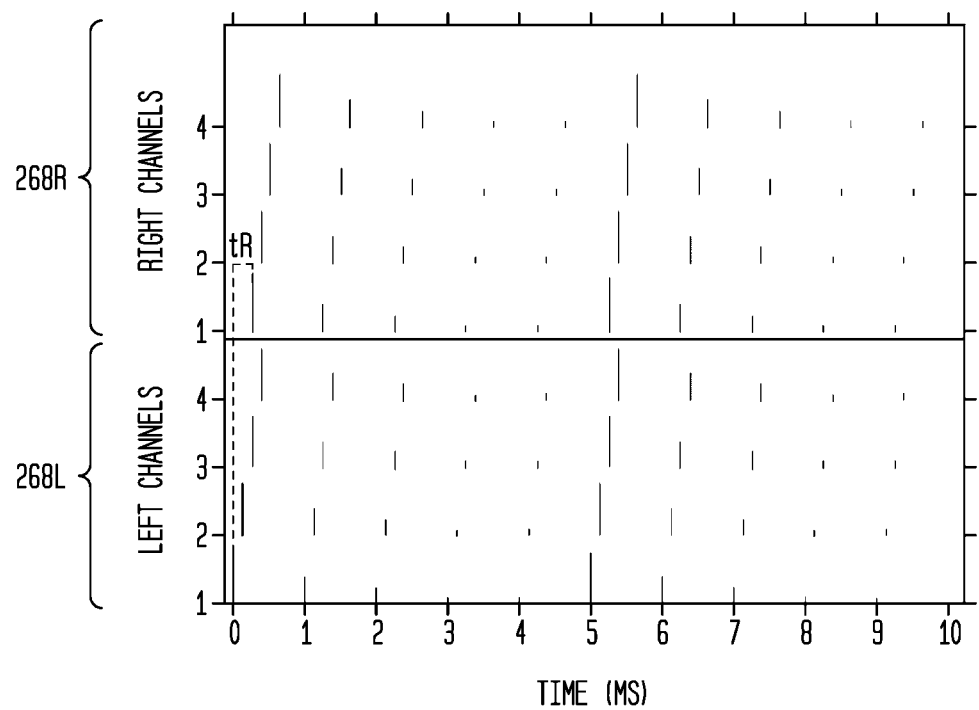
FIG. 3 is a schematic diagram illustrating stimulation pulse timing of a cochlear implant system, in accordance with certain embodiments presented herein.

FIG. 3 is a diagram illustrating one example stimulation pulse sequence 268L and an example stimulation pulse sequence 268R generated by cochlear implants 202L and 202R, respectively, in accordance with embodiments presented herein. For ease of illustration and clarity, only four channels are shown. However, as noted above, a typical cochlear implant system may have anywhere from 12 to 22 channels, although other numbers of channels are possible. In FIG. 3, the channel stimulation rate is 1000 pulses per second (pps) and there is a single dominant sound source, which has an F0 of 200 Hz. As such, the modulating signals 259L (mL) and 259R (mR) each have a period of 5 milliseconds (ms). Additionally, the dominant sound source is on the left side of the recipient's head (i.e., proximate to cochlear implant 202L), with an ITD at the right cochlear implant 202R of 250 microseconds (µs). As such, the pulses in the stimulation pulse sequence 268R delivered to the recipient's right-side cochlea by cochlear implant 202R are delayed by 250 µs relative to the pulses in the stimulation pulse sequence 268L delivered to the recipient's left-side cochlea by cochlear implant 202L. In FIG. 3, the delay is labelled as "tR."

In summary, FIGS. 2 and 3 illustrate embodiments in which cochlear implants 202L and 202R generate stimulation pulse sequences 268L and 268R, respectively, with a same amplitude modulation based on the fundamental frequency (F0) of the one or more sound sources 221 (i.e., cochlear implants 202L and 202R synchronize the modulation of the stimulation pulse amplitudes in the first and second pulse sequences 268L and 268R). In FIG. 2, the same modulation applied at both of the cochlear implants 202L and 202R is based on the full ipsilateral and the full contralateral audio data (i.e., based on the first set of sound signals 248L and the second set of sound signals 248R), which is exchanged between the cochlear implants.

Additionally, in the embodiments of FIGS. 2 and 3, the cochlear implants 202L and 202R are configured to synchronize, in time, the delivery of the stimulation pulse sequences 268L and 268R to the recipient based on the relative location of the one or more sound sources 221. Again, the relative timing at which the stimulation pulse sequences 268L and 268R are delivered to the recipient is determined based on the full ipsilateral and the full contralateral audio data (i.e., based on the first set of sound signals 248L and the second set of sound signals 248R), which is exchanged between the cochlear implants. The relative timing between the stimulation pulse sequences 268L and 268R corresponds to the ITD the first set of sound signals 248L and the second set of sound signals 248R (i.e., the delay between the which the first set of sound signals 248L and the second set of sound signals 248R are received at the cochlear implants 202L and 20R, or vice versa). As a result, bilateral cochlear implant system 200 is configured to both improve pitch perception (via the synchronized (the same) F0 amplitude modulation) and to provide appropriate ITD cues (via the synchronized timing of the delivery of the stimulation pulse sequences 268L and 268R to the recipient).

In certain embodiments of FIG. 2, the delay between the delivery of the stimulation pulse sequences 268L and 268R may directly correspond to the determined ITD. However, in certain embodiments, the ITD cues (relative delay between delivery of the pulse sequences 268L and 268R) can be exaggerated, compensating for the reduced sensitivity of cochlear recipients to ITD cues. For example, the relative delay between delivery of the pulse sequences 268L and 268R may be larger than the estimated ITD, such as a multiple of the actual ITD (e.g., the pulse delay could be twice the estimated ITD).

Additionally or alternatively, the ILD cues could be exaggerated by the mixers 256L or 256R by applying an additional gain or attenuation to the modulated envelopes 261L or 261R (v4L or v4R) on the appropriate side. That is, in such embodiments, the delay signals 267L and 267R are also applied to the mixers 256L and 256R, respectively. As a result, the mixers 256L or 256R can adjust the gain or attenuation applied to the modulated envelopes 261L or 261R based on the ITD (as represented in the delay signals 267L and 267R).

Figure 4:
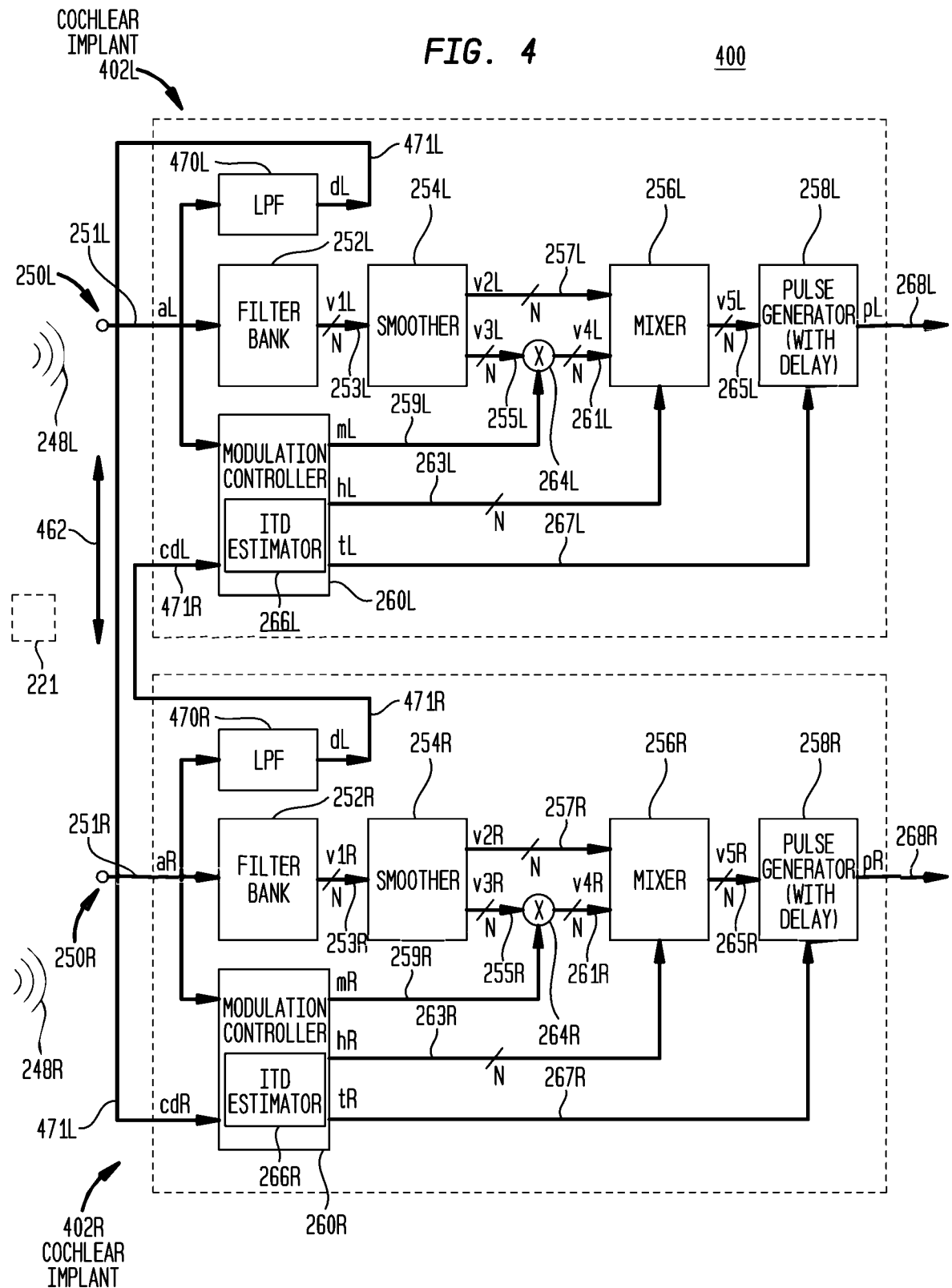
FIG. 4 is a functional block diagram of another cochlear implant system, in accordance with certain embodiments presented herein.

As noted, FIG. 2 illustrates an embodiment in which the cochlear implants 202L and 202R exchange the audio data 251L and 251R. FIG. 4 illustrates an alternative embodiment in which signals, which are lower bandwidth than the audio data 251L and 251R, are exchanged between two cochlear implants, in accordance with embodiments presented herein.

More specifically, shown in FIG. 4 is a cochlear implant system 400 comprising a left (first) cochlear implant 402L and a right (second) cochlear implant 402R. Cochlear implant 402L is similar to cochlear implant 202L and comprises a microphone array 250L (e.g., dual-microphone system), a filterbank 252L, a smoother 254L, a mixer 256L, a pulse generator 258L, and a modulation controller 260L. However, cochlear implant 402L also comprises a low-pass filter 470L.

Cochlear implant 402R is similar to cochlear implant 202R and comprises a microphone array 250R (e.g., dual-microphone system), a filterbank 252R, a smoother 254R, a mixer 256R, a pulse generator 258R, and a modulation controller 260R. However, cochlear implant 402R also comprises a low-pass filter 470R.

Unless noted below, components/blocks in FIG. 4 with similar numbering to components/blocks in FIG. 2 may perform a substantially similar function as the same similarly number component/block of FIG. 2. However, as detailed below, the components/blocks in FIG. 4 may operate based on similar, but slightly different inputs, than the same similarly numbered component/block of FIG. 2.

Moreover, unless noted below, signals and/or sets of signal sets with similar numbering to signals and/or sets of signal sets in FIG. 2 may be substantially similar to the same similarly number signals and/or sets of signal sets of FIG. 2. However, as detailed below, the signals and/or sets of signals FIG. 4 may be generated based on similar, but slightly different inputs, than the same similarly numbered signals and/or sets of signals of FIG. 2.

As noted above, acoustic sound signals (sounds) 248L are received at the microphone array 250L, while acoustic sound signals (sounds) 248R are received at the microphone array 250L. The acoustic sound signals 248L and 248R are used to generate audio data (aL) 251L and 251R, respectively.

As described above with reference to FIG. 2, the audio data 251L and 251R are applied to filterbanks 252L and 252R, respectively, which generate filterbank envelopes 253L (v1L) and filterbank envelopes 253R (v1R), respectively. Similarly, the audio data 251L and 251R are applied to the modulation controllers 260L and 260R, respectively.

In the specific example of FIG. 4, the audio data 251L and 251R are also applied to the low-pass filters 470L and 470R, respectively. The acoustic sound signal 251L is applied to the low-pass filter 470L to generate a low-frequency audio data 471L. That is, low-frequency audio data 471L represents only low frequency portion of the audio data 251L. Similarly, the audio data 251R is applied to the low-pass filter 470R to generate low-frequency audio data 471R. That is, low-frequency audio data 471R represents only a low frequency portion of the audio data 251R.

FIG. 4 illustrates an example arrangement in which the low-pass filters 470L and 470R are separate from the filterbanks 252L and 252R, respectively. However, in an alternative embodiment, the low-pass filters 470L and 470R may be implemented by collecting the outputs from a small number (e.g., 2, 3, or 4) of the lowest frequency band-pass filters in the filterbanks 252L and 252R, respectively. That is, the outputs from a small number of the filterbanks 252L can be summed to generate low-frequency audio data 471L, while a small number of the filterbanks 252R can be summed to generate low-frequency audio data 471R.

In the example of FIG. 4, cochlear implants 402L and 402R are configured to operate a two-way audio link/channel 462 that enables the transfer of low-frequency audio data 471L and 471R between the cochlear implants. That is, the two-way audio channel 462 enables the cochlear implant 402R to send low-frequency audio data 471R to cochlear implant 402L and, similarly, enables cochlear implant 402L to send low-frequency audio data 471L to cochlear implant 402R. The two-way audio channel 462 may be a digital wired electrical channel or a digital wireless channel (e.g., a standardized wireless channel, such as Bluetooth®, Bluetooth® Low Energy (BLE) or other channel interface making use of any number of standard wireless streaming protocols; a proprietary protocol for wireless streaming of the audio data; etc. Bluetooth® is a registered trademark owned by the Bluetooth® SIG).

As noted above, in the example of FIG. 2, the cochlear implants 202L and 202R exchange the complete audio data 251L and 251R with one another. In contrast, in the example of FIG. 4, the cochlear implants 402L and 402R only exchange a frequency-limited portion of the audio data 251L and 251R with one another (i.e., low-frequency audio data 471L and 471R). As such, the low-frequency audio data 471L and 471R can be transmitted digitally (e.g. wirelessly) using a lower data rate than the original audio data 251L and 251R, which has the benefit of reducing power consumption.

In FIG. 4, the audio data 251L and the low-frequency audio data 471R (received directed or received via the two-way audio channel 462) are applied to each of the modulation controllers 260L and 260R. In general, the modulation controllers 260L and 260R operate, as described above, to generate modulator signals 259L (mL) and 259R (mR), respectively, that each have a period corresponding to the fundamental frequency (F0) of the most dominant harmonic component in the audio data 251L and 251R. That is, the modulation controllers 260L and 260R are each configured to identify the fundamental frequency (F0) associated with received sound signals 248L and 248R. The modulation controllers 260L and 260R then generate the modulation signals 259L and 259R, respectively, based on the identified fundamental frequency (F0).

In the example of FIG. 4, the modulation controllers 260L and 260R operate on both the ipsilateral (same side) audio data 251L and the contralateral (other side) low-frequency audio data 471R or 472R (lower-bandwidth signals). In certain embodiments, modulation controller 260L is configured to generate a first estimate of the fundamental frequency, referred to as "$F0_{iL}$," using the ipsilateral audio data 251L and a second estimate of the fundamental frequency, referred to as "$F0_{cL}$," using the contralateral low-frequency audio data 471R. If the two estimates $F0_{iL}$ and $F0_{cL}$ are approximately equal, then it is assumed that there is one dominant sound source in the environment, and binaural processing functions in accordance with embodiments presented are enabled. Conversely, if the two estimates $F0_{iL}$ and $F0_{cL}$ are significantly different, then it is assumed that there is not a single dominant sound source, and the binaural processing functions in accordance with embodiments presented herein disabled. The modulation controller 260R may operate in a similar to manner to generate and compare two estimates of the fundamental frequency, referred to as "$F0_{iR}$" (made using the ipsilateral audio data 251R) and $F0_{cR}$" (made using the contralateral low-frequency audio data 471L).

The modulation controllers 260L and 260R will each reach the same conclusion regarding whether or not to disable the binaural processing functions in accordance with embodiments presented are enabled. That is, the lower-bandwidth signals 471L and 471R still allows the common F0 and ITD to be estimated by the modulation controllers 260L and 260R.

When not disabled, the cochlear implants 402L and 402R will each operate as described above with reference to FIG. 2 in order to generate the stimulation pulse sequences 268L and 268R, respectively. As above, the stimulation pulse sequences 268L and 268R are generated using the same amplitude modulation (using the same modulation function corresponds to F0 of the one or more sound sources 221). However, depending on the location of the most dominant harmonic sound source, the stimulation pulses in either stimulation pulse sequence 268R or 268L may be time delayed relative to the other, where the time delay is based on an estimate of the ITD for the most dominant harmonic sound source.

In summary, FIG. 4 illustrates an arrangement that is substantially similar to that of FIG. 2. However, whereas in FIG. 2 the cochlear implants 202L and 202R exchange the full audio data 251L and 251R, the cochlear implants 402L and 402R only exchange low-frequency portions of the audio data 251L and 251R. Thereafter, cochlear implants 402L and 402R operate as described with reference to FIG. 2 in order to generate the pulse sequences 268L and 268R delivered to the left and right ears, respectively, of the recipient.

Figure 5:
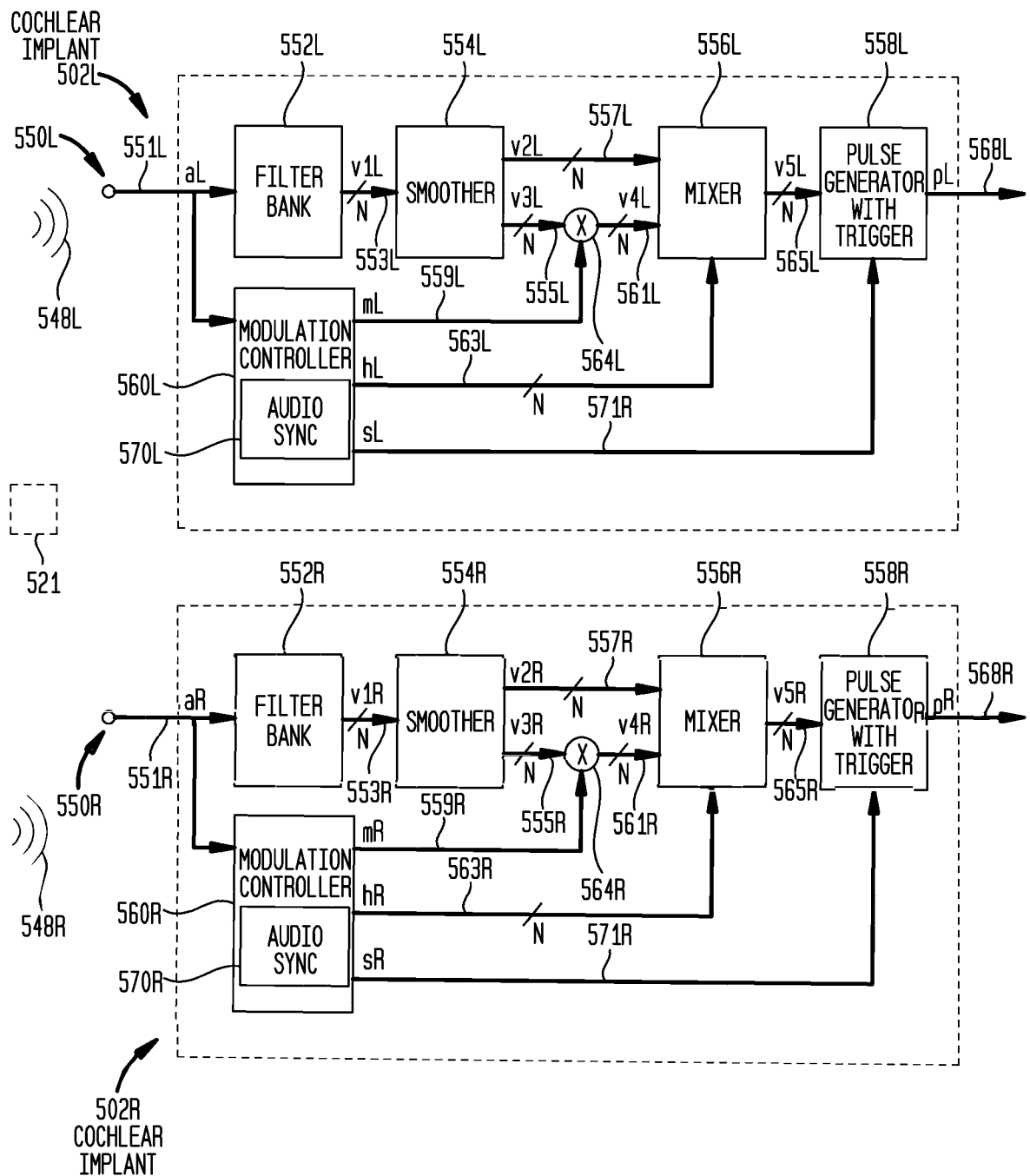
FIG. 5 is a functional block diagram of another cochlear implant system, in accordance with certain embodiments presented herein.

As noted above, the embodiments of FIGS. 2 and 4 generally rely on the bi-directional exchange of audio data between the bilateral cochlear implants. FIG. 5 illustrates another embodiment that does not rely upon a bi-directional exchange of audio data. As described further below, the cochlear implants of FIG. 5 are each configured to derive a synchronization signal from the ipsilateral audio data only and use this synchronization signal to control the pulse timing to preserve ITD information.

More specifically, FIG. 5 is a functional block diagram of a bilateral cochlear implant system 500 in accordance with embodiments presented herein. As shown, the bilateral cochlear implant system 500 comprises a left (first) cochlear implant 502L and a right (second) cochlear implant 502R. Referring first to cochlear implant 502L, the cochlear implant comprises a microphone array 550L (e.g., dual-microphone system), a filterbank 552L, a smoother 554L, a mixer 556L, a pulse generator 558L, and a modulation controller 560L.

In certain examples, the operations described below with reference to filterbank 552L, smoother 554L, mixer 556L, and modulation controller 560L may be performed at a processing module, such as processing module 124L of FIG. 1D. Additionally, in certain examples, certain operations described below with reference to pulse generator 558L may be performed at a processing module (e.g., processing module 124L), while other operations may be performed at a stimulator unit, such as stimulator unit 142L of FIG. 1D.

Cochlear implant 502R, which is substantially similar to cochlear implant 502L, comprises a microphone array 550S, a filterbank 552R, a smoother 554R, a mixer 556R, a pulse generator 558R, and a modulation controller 560R. In certain examples, the operations described below with reference to filterbank 552R, smoother 554R, mixer 556R, and modulation controller 560R may be performed at a processing module, such as processing module 124R of FIG. 1E. Additionally, in certain examples, certain operations described below with reference to pulse generator 558R may be performed at a processing module (e.g., processing module 124R), while other operations may be performed at a stimulator unit, such as stimulator unit 142R of FIG. 1E.

Although FIG. 5 will be described with reference to the use of microphone arrays 550L and 550R, it is to be appreciated that the cochlear implants 502L and 502R may also or alternatively include different types and combinations of sound input devices. It is also to be appreciated that the functional blocks shown in FIG. 5 for each of cochlear implants 502L and 502 may be distributed across one, two, or more different physical devices. For example, certain functional blocks shown in FIG. 5 for cochlear implant 502L may be part of an external component (e.g., external component 104L), while other functional blocks for cochlear implant 502L may be part of an implantable component (e.g., implantable component 112L). Alternatively, all of the functional blocks for cochlear implant 502L may be part of an implantable component, the functional blocks for cochlear implant 502L may be split between two external components and an implantable component, etc.

Returning to the example of FIG. 5, a first set of acoustic sound signals (sounds) 548L are received at the microphone array 550L and are used to generate audio data (aL) 551L. More specifically, the audio data 551L is derived from microphone signals, processed by analog-to-digital converters (ADC), a beamformer, and an Automatic Gain Control (AGC), all of which have been omitted from FIG. 5 for ease of illustration. Due, in part, to the use of different stimulation channels to deliver stimulation to the recipient, the audio data 551L is applied to the filterbank 552L, which comprises a band-pass filter and an envelope detector for each of a plurality of stimulation channels. As such, the filterbank 552L produces a set (e.g., a plurality) of filterbank envelopes 553L (v1L), where each filterbank envelope is associated with a stimulation channel. In a similar manner, microphone array 550R converts a second set of acoustic sound signals (sounds) 548R are into audio data (aR) 551R.

Similar to the above embodiments, the lines/arrows marked by "/N" in FIG. 5, such as arrows 553L and 553R, indicate sets of related signals, with one signal for each of a plurality of stimulation channels in the cochlear implant system. A typical cochlear implant system may have between 12 and 22 stimulation channels, although other numbers of channels may be used in different embodiments.

The filterbank envelopes 553L and 553R are applied to the smoothers 554L and 554R, respectively, which smooth each of the filterbank envelopes to remove amplitude fluctuations having frequencies within and above an expected range of fundamental frequencies. The smoothers 554L and 554R produce a set of smoothed envelope signals 555L (v3L) and 55R (v3R), respectively.

Additionally, the smoothers 554L and 554R delay the set of filterbank envelopes 553L and 553R, respectively, to produce a set of delayed filterbank envelopes 557L (v2L) and 557R (v2R), respectively, with a delay that matches the inherent delay that is introduced by the smoothing operations of smoother 554L and 554R, respectively. In other words, envelopes 555L and 557L are aligned in time and the envelopes 555R and 557R are aligned in time.

As noted elsewhere herein, the first set of acoustic sound signals 548L and the second set of acoustic sound signals 548R are generated by the same one or more sound sources 521. As such, the set of acoustic sound signals 548L and the second set of acoustic sound signals 548R are received "contemporaneously" (i.e., around the same time) by the cochlear implants 502L and 502R. However, the first set of acoustic sound signals 548L and the second set of acoustic sound signals 548R are received at the respective cochlear implants 502L and 502R with a relative timing that corresponds to the location of the one or more sound sources 521. In other words, one of either the first or second set of acoustic sound signals may be received with a delay, relative to the receipt of the other of first or second set of acoustic sound signals. The delay corresponds to the Interaural Time Difference (ITD) between the left and right ears of the recipient, relative to the location of the one or more sound sources. The ITD may change (increase or decrease) as the location of the one or more sound sources 511 changes.

In the example of FIG. 5, the audio data 551L is also applied to the modulation controller 560L, while the audio data 55R is applied to the modulation controller 560R. In general, the modulation controllers 560L and 560R are each configured to generate a modulator signal 559L (mL) and 559R (mR) that each have a period corresponding to the fundamental frequency (F0) of the most dominant harmonic component in the audio data 551L and 551R. That is, the modulation controller 560L is configured to identify the fundamental frequency (F0) associated with received sound signals 548L, while the modulation controller 560R is configured to identify the fundamental frequency (F0) associated with received sound signals 548R. The modulation controllers 560L and 560R then generate the modulation signals 559L and 559R, respectively, based on the identified fundamental frequency (F0).

In addition to generating modulator signals 559L and 559R, the modulation controllers 560L and 560R are each configured to generate an estimate, for each of the plurality of band-pass filter channels, of the probability that the signal component in the corresponding band-pass filter channel is harmonically related to the dominant harmonic component in the audio data 551L and 551R. As such, the modulation controller 560L generates a set 563L of harmonic probability signals (hL) and modulation controller 560R generates a set 563R of harmonic probability signals (hR). Each signal in the sets 563L and 563R correspond to one of the band-pass filter channels and provide an estimate of the probability that the signal in that corresponding band-pass filter channel is harmonically related to the dominant harmonic component in audio data 551L and 551R.

The sets 563L and 563R of harmonic probability signals are applied to the mixers 556L and 556R, respectively. The mixer 556L is configured to sum the delayed filterbank envelopes 557L (v2L) and the modulated envelope signals 561L (v4L), with the relative proportions of each controlled by the harmonic probability signals in set 561L. The mixer 556L produces a set of output envelopes (v5L) 565L. The set of output envelopes 565L are then applied to the pulse generator 558L. Mixer 556R operates in a similar manner to sum the delayed filterbank envelopes 557R (v2R) and the modulated envelope signals 561R (v4R), with the relative proportions of each controlled by the harmonic probability signals in set 561R. The mixer 556R produces a set 565R of modulated output envelopes (v5R). The set 565R of modulated output envelopes are then applied to the pulse generator 558R.

As noted above, the embodiments of FIGS. 2 and 4 each utilize an ITD estimator in the respective modulation controllers to estimate the ITD of the most dominant harmonic component in the ipsilateral and contralateral audio data. However, in the embodiment of FIG. 5, the cochlear implants 502L and 502L operate using only the ipsilateral audio data (e.g., the audio data received at the respective microphone arrays 550L and 550B, respectively). As such, since the cochlear implants 502L and 502L do not have the contralateral audio data, the cochlear implants 502L and 502L do not estimate the ITD directly from the audio data. Instead, in the embodiment of FIG. 5, the cochlear implants 502L and 502L are each configured to derive a synchronization signal from the ipsilateral audio data only and use this synchronization signal to control the pulse timing to preserve ITD information.

Referring specifically to cochlear implant 502L, the modulation controller 560L includes an audio synchronizer 570L that generates a synchronization signal 571L (sL) from the audio data 551L. In accordance with embodiments presented herein, the synchronization signal 571L goes active at the start of each fundamental period of the modulation signal 559L (i.e., once every T0 seconds, where T0=1/F0). The synchronization signal 571L is applied to the pulse generator 558L such that each activation of the synchronization signal 571L triggers the pulse generator 558L to generate a sequence of pulses of duration T0 and with the modulation of F0, as described above. That is, synchronization signal 571L initiates the start of a sequence of F0 modulated pulses, where the sequence has a duration of T0.

Figure 6A:
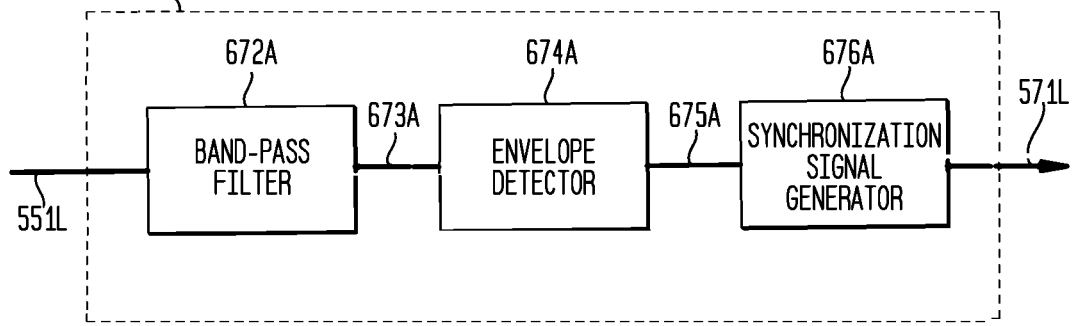
FIG. 6A is a functional block diagram of an audio synchronizer of a cochlear implant system, in accordance with certain embodiments presented herein.
Figure 6B:
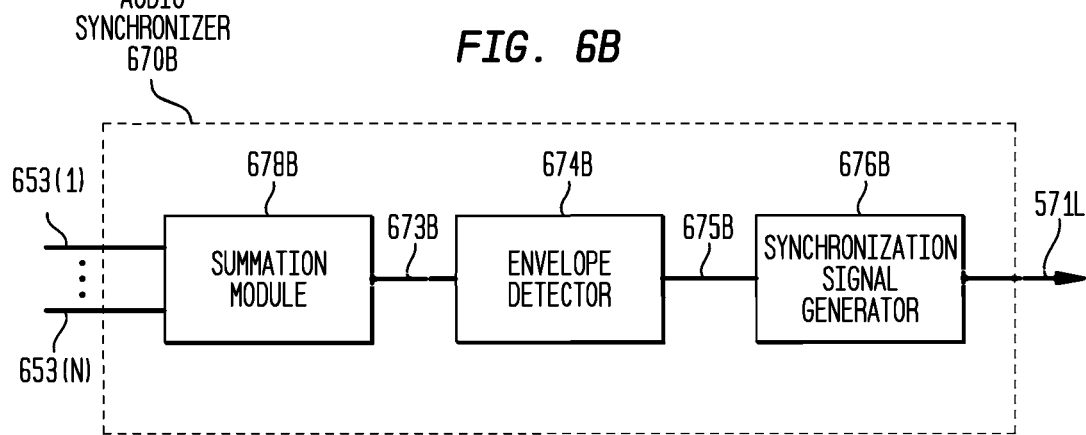
FIG. 6B is a functional block diagram of another audio synchronizer of a cochlear implant system, in accordance with certain embodiments presented herein.
Figure 6C:
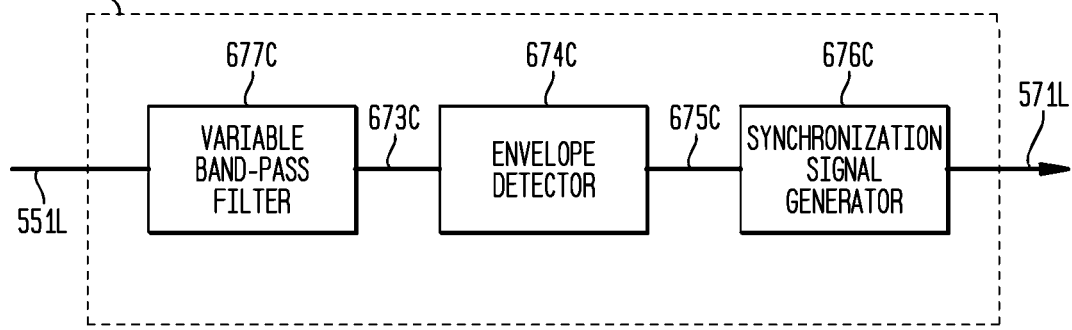
FIG. 6C is a functional block diagram of another audio synchronizer of a cochlear implant system, in accordance with certain embodiments presented herein.

The audio synchronizer 570L may use any of a number of different methods to generate the synchronization signal 571L. FIGS. 6A-6C are block diagrams illustrating example methods that may be performed by the cochlear implant 502L (e.g., audio synchronizer 570L) to generate the synchronization signal 571L.

Referring first to FIG. 6A, shown is a first embodiment for the audio synchronizer 570L, referred to as audio synchronizer 670A, in which a band-pass filter 672A spanning a low frequency range (e.g., about 70 Hz to about 500 Hz) is applied to the audio data 551L (FIG. 5). Application of the band-pass filter 672A to the audio data 551L generates an auxiliary signal 673A that includes multiple harmonics of the dominant harmonic sound source. As a result, the envelope of the auxiliary signal 673A will modulate at F0. As shown in FIG. 6A, an envelope detector 674A applies envelope detection to the auxiliary signal 673A to produce an auxiliary envelope signal 675A. A synchronization signal generator 676A then derives the synchronization signal 571L (FIG. 5) from one or more particular attributes of the auxiliary envelope signal 675A. For example, in one embodiment, the synchronization signal generator 676A derives the synchronization signal 571L from the positive peaks of the auxiliary envelope signal 675A. The peak detection process can utilize the estimated F0, and hence the estimated period T0, to avoid spurious/false peaks. In an alternative example, the synchronization signal generator 676A derives the synchronization signal 571L from the negative peaks (i.e. troughs) of the auxiliary envelope signal 675A.

In a still other embodiment, the synchronization signal generator 676A includes a high-pass filter having a low corner frequency (e.g., about 50 Hz). In this embodiment, the high-pass filter is applied to the auxiliary envelope signal 675A to remove the low-frequency component of the envelope. The synchronization signal generator 676A may then detect and utilize positive zero-crossings and/or negative zero-crossings to generate the synchronization signal 571L.

FIG. 6B illustrates another embodiment for the audio synchronizer 570L, referred to as audio synchronizer 670B, in which outputs (filterbank envelopes) from a selected number (e.g., 2, 3, or 4) of the lowest frequency band-pass filters in the filterbank 552L (FIG. 5) are obtained. In FIG. 6B, the filterbank envelopes from the selected number of the lowest frequency band-pass filters in the filterbank 552L are represented by arrows 653(1)-665(N).

The filterbank envelopes 653(1)-665(N) are summed at summation module (summer) 678B to generate an auxiliary signal 673B that includes multiple harmonics of the dominant harmonic sound source. As a result, the envelope of the auxiliary signal 673B will modulate at F0. As shown in FIG. 6B, an envelope detector 674B applies envelope detection to the auxiliary signal 673B to produce an auxiliary envelope signal 675B. A synchronization signal generator 676B then derives the synchronization signal 571L (FIG. 5) from one or more signal attributes (one or more attributes) of the auxiliary envelope signal 675B. In general, the synchronization signal generator 676B may operate similarly to synchronization signal generator 676A, described above with reference to FIG. 6A, to generate the synchronization signal 571L from one or more attributes of the auxiliary envelope signal 675B (e.g., from the positive peaks, the negative peaks, he positive zero-crossings, negative zero-crossings, etc.).

FIG. 6C illustrates another embodiment for the audio synchronizer 570L, referred to as audio synchronizer 670C, in which a variable band-pass filter 677C is applied to the audio data 551L (FIG. 5). The variable band-pass filter 677C has a center frequency is set to pass the estimated F0, and an upper cut-off frequency that is set to block a frequency of twice F0.

Application of the variable band-pass filter 677C to the audio data 551L generates an auxiliary signal 673C that includes substantial energy from the fundamental component, but little energy from the higher harmonics. As shown in FIG. 6C, an envelope detector 674C applies envelope detection to the auxiliary signal 673C to produce an auxiliary envelope signal 675C. A synchronization signal generator 676C then derives the synchronization signal 571L (FIG. 5) from one or more attributes of the auxiliary envelope signal 675C. In general, the synchronization signal generator 676C may operate similarly to synchronization signal generator 676A, described above with reference to FIG. 6A, to generate the synchronization signal 571L from one or more attributes of the auxiliary envelope signal 675C (e.g., from the positive peaks, the negative peaks, the positive zero-crossings, the negative zero-crossings, etc.).

Returning to the specific example of FIG. 5, the cochlear implant 502R also includes a modulation controller 560R with an audio synchronizer 570R. The audio synchronizer 570R may operate, for example, as described above with reference to FIGS. 6A-6C to generates a synchronization signal 571R (sR) from the audio data 551R. In accordance with embodiments presented herein, the synchronization signal 571R goes active at the start of each fundamental period of the modulation signal 559R (i.e., once every T0 seconds, where T0=1/F0). The synchronization signal 571R is applied to the pulse generator 558R such that each activation of the synchronization signal 571R triggers the pulse generator 558R to generate a sequence of pulses of duration T0 and with the modulation of F0, as described above. That is, synchronization signal 571R initiates the start of a sequence of F0 modulated pulses, where the sequence has a duration of T0.

In the embodiment of FIG. 5, in response to a harmonic audio source in the audio environment, the bilateral cochlear implant system 500 will obtain audio data 551L at the left ear and audio data 551R at the right ear, whereby the corresponding harmonic components of the audio data 551L and 551R will have an ITD that is dependent on the location of the audio source. Because, as detailed above, the timing of each synchronization signal 571L and 571R is directly related to the temporal features of the dominant harmonic component in the corresponding audio data 551L and 5518, the same ITD will be present between the synchronization signals 571L and 571R, and thus also between the pulses sequence 568L delivered via the left cochlear implant 502L, and the pulse sequence 568R delivered via the right cochlear implant 502R.

That is, as noted above, the synchronization signals 571L and 571R are activated (generated) based on the same parameters of the audio data 551L and 551R. These parameters will occur in 551L and 551R with a relative time difference that corresponds to the ITD. For example, if the dominant sound source is on the left, the features will appear in 551L before the same features appear in 551R. The time period between when the features occur in 551L and when the features appear in 551R corresponds to the ITD. Therefore, since the synchronization signals 571L and 571R are activated based on these features (which are appear in 551R after 551L at a time delay corresponding to the ITD), then the synchronization signal 571R will also be activated a time period after synchronization signal 571L, where the delay between signals 571L and 571R corresponds to the ITD. Again, since the synchronization signals 571L and 571R control when pulses in the pulses sequences 568L and 568R will be generated, each group of pulses generated at 558R will be delayed relative to each group of pulses generated at 558L, at least until the ITD of the input audio changes. The result again is pulse sequences such as those shown in FIG. 3.

In summary, FIGS. 5 and 6A-6C illustrate embodiments in which cochlear implants 502L and 502R generate stimulation pulse sequences 568L and 568R, respectively, with an amplitude modulation that is based on the fundamental frequency (F0) of the one or more sound sources 521 (i.e., the cochlear implants 502L and 502R synchronize the modulation of the stimulation pulse amplitudes in the first and second pulse sequences 568L and 568R). In FIG. 5, the modulation applied at both of the cochlear implants 502L and 502R is based on the ipsilateral audio data only (i.e., based on only the first set of sound signals 548L at cochlear implant 502L and based on only the second set of sound signals 548R at cochlear implant 502R).

Additionally, in the embodiments of FIGS. 5 and 6A-6C, the cochlear implants 502L and 502R are configured to synchronize, in time, the delivery of the stimulation pulse sequences 568L and 568R to the recipient based on the relative location of the one or more sound sources 521. Again, the relative timing at which the stimulation pulse sequences 568L and 568R (i.e., time delay between delivery of the pulse sequences) is determined from the ipsilateral audio data only (i.e., based on only the first set of sound signals 548L at cochlear implant 502L and based on only the second set of sound signals 548R at cochlear implant 502R). In particular, each of the cochlear implants 502L and 502R synchronize the timing of the delivery of the stimulation pulse sequences 568L and 568R to the recipient based on one or more attributes occurring in both of the first and second sets of sound signals 548L and 548R, wherein the one or more attributes occur in the first and second sets of sound signals 548L and 548R with a relative timing corresponding to the ITD (i.e., the one or more attributes may be delayed in one of the first or second sets of sound signals 548L and 548R relative to the other of the first or second sets of sound signals 548L and 548R). As a result, the relative timing between the delivery of the stimulation pulse sequences 568L and 568R corresponds to the ITD the first set of sound signals 548L and the second set of sound signals 548R (i.e., the delay between the which the first set of sound signals 548L and the second set of sound signals 548R are received at the cochlear implants 502L and 50R, or vice versa). As a result, bilateral cochlear implant system 500 is configured to both improve pitch perception (via the synchronized (the same) F0 amplitude modulation) and to provide appropriate ITD cues (via the synchronized timing of the delivery of the stimulation pulse sequences 568L and 568R to the recipient).

FIG. 7 is a flowchart of a method 780 in accordance with certain embodiments presented herein. Method 780 begins at 781 where a first cochlear implant of a bilateral cochlear implant system receives a first set of sound signals. At 782, a second cochlear implant of the bilateral cochlear implant system receives a second set of sound signals, wherein the first set of sound signals and the second set of sound signals are associated with a same one or more sound sources. At 783, the first cochlear implant generates a first sequence of stimulation pulses based on the first set of sound signals, wherein the first sequence of stimulation pulses have amplitudes that are modulated with a first modulation. At 784, the first cochlear implant delivers the first sequence of stimulation pulses to a first ear of a recipient of the bilateral cochlear implant system. At 785, the second cochlear implant generates a second sequence of stimulation pulses based on the second set of sound signals, wherein the second sequence of stimulation pulses have amplitudes that are modulated using the same first modulation as the first sequence of stimulation pulses. At 786, the second cochlear implant delivers the second sequence of stimulation pulses to a second ear of the recipient. The second sequence of stimulation pulses is delivered to the recipient with a time delay relative to delivery of the first sequence of stimulation pulses and wherein the time delay is based on an Interaural Time Difference (ITD) associated with receipt of the first set of sound signals at the first cochlear implant and receipt of the second set of sound signals at the second cochlear implant.

FIG. 8 is a flowchart of a method 890 in accordance with certain embodiments presented herein. Method 890 begins at 891 where a first cochlear implant of a bilateral cochlear implant system receives first audio data (e.g., a first set of sound signals). At 892, the second cochlear implant of the receives second audio data (e.g., a second set of sound signals) at a second cochlear implant of the bilateral cochlear implant system, wherein the first and second audio data are associated with a same fundamental frequency. At 893, the first cochlear implant generates a first sequence of stimulation pulses representative of the first audio data and, at 894, the first cochlear implant amplitude modulates the first sequence of stimulation pulses based on the fundamental frequency of the first audio data and second audio data. At 895, the second cochlear implant generates a second sequence of stimulation pulses representative of the second audio data and, at 896, the second cochlear implant amplitude modulates the second sequence of stimulation pulses based on the fundamental frequency of the first audio data and second audio data. At 897, a timing of delivery of the first sequence of stimulation pulses to a first ear of a recipient of the bilateral cochlear implant system is synchronized with a timing of delivery of the second sequence of stimulation pulses to a second ear of the recipient of the bilateral cochlear implant system.

Merely for ease of description, the techniques presented herein have primarily described herein with reference to an illustrative medical device system, namely a bilateral cochlear implant system that delivers electrical stimulation to both ears of a recipient. However, it is to be appreciated that the techniques presented herein may also be used with a variety of other medical devices that, while providing a wide range of therapeutic benefits to recipients, patients, or other users, may benefit from the techniques presented. For example, a bilateral cochlear implant system in accordance with embodiments presented herein may also deliver acoustic stimulation to one or both ears of the recipient (e.g., one or more of the cochlear implants is an electro-acoustic cochlear implant). It is also to be appreciated that the two cochlear implants of a bilateral cochlear implant system in accordance with embodiments presented need not be identical with respect to, for example, the number of electrodes used to electrically stimulate the cochlea, the type of stimulation delivered, etc. Furthermore, it is to be appreciated that the techniques presented herein may be used with other binaural hearing prosthesis systems, such as systems including acoustic hearing aids, bone conduction devices, middle ear auditory prostheses, direct acoustic stimulators, other electrically simulating auditory prostheses (e.g., auditory brain stimulators), etc. The techniques presented herein may also be used with vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation, etc.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   receiving first audio data at a first device of a bilateral system;
   receiving second audio data at a second device of the bilateral system, wherein the first and second audio data are associated with a same fundamental frequency;
   generating, at the first device, a first sequence of stimulation pulses representative of the first audio data;
   amplitude modulating the first sequence of stimulation pulses based on the fundamental frequency of the first audio data and second audio data;
   generating, at the second device, a second sequence of stimulation pulses representative of the second audio data;
   amplitude modulating the second sequence of stimulation pulses based on the fundamental frequency of the first audio data and second audio data; and
   synchronizing a timing of delivery of the first sequence of stimulation pulses to a first ear of a recipient of the bilateral system with a timing of delivery of the second sequence of stimulation pulses to a second ear of the recipient of the bilateral system.

2. The method of claim 1, wherein the fundamental frequency is related to one or more sound sources in an audio environment of the recipient, and wherein synchronizing the timing of delivery of the first sequence of stimulation pulses with the timing of delivery of the second sequence of stimulation pulses comprises:
   synchronizing the timing of the delivery of the first sequence of stimulation pulses to the first ear of the recipient with the timing of delivery of the second sequence of stimulation pulses to the second ear of the recipient based on a relative location of the one or more sound sources in the audio environment.

3. The method of claim 1, wherein synchronizing the timing of delivery of the first sequence of stimulation pulses with the timing of delivery of the second sequence of stimulation pulses comprises:
   synchronizing the timing of the delivery of the first sequence of stimulation pulses and the second sequence of stimulation pulses based on one or more signal attributes occurring in both of the first audio data and the second audio data.

4. The method of claim 3, wherein the one or more signal attributes occur in the first audio data and the second audio data with a relative timing corresponding to an Interaural Time Difference (ITD) associated with receipt of the first audio data at the first device and receipt of the second audio data at the second device.

5. The method of claim 3, further comprising:
   detecting, at the first device, one or more signal attributes of the first audio data;
   detecting, at the second device, one or more signal attributes of the second audio data, wherein the one or more signal attributes of the second audio data are the same one or more signal attributes of the first audio data;
   setting a timing of the delivery of the first sequence of stimulation pulses to the first ear of the recipient based on a timing of the one or more signal attributes in the first audio data; and
   setting a timing of the delivery of the second sequence of stimulation pulses to the second ear of the recipient based on a timing of the one or more signal attributes in the second audio data.

6. The method of claim 1, wherein synchronizing the timing of delivery of the first sequence of stimulation pulses to the first ear of the recipient with the timing of delivery of the second sequence of stimulation pulses to the second ear of the recipient comprises:
   delivering the second sequence of stimulation pulses to the second ear of the recipient with a time delay, relative to delivery of the first sequence of stimulation pulses to the first ear of the recipient.

7. The method of claim 6, wherein the time delay for delivery of the second sequence of stimulation pulses relative to the delivery of the first sequence of stimulation pulses is substantially equal to an Interaural Time Difference (ITD) associated with receipt of a first audio data at the first device and receipt of the second audio data at the second device, respectively.

8. The method of claim 7, further comprising:
   determining the timing of the delivery of the second sequence of stimulation pulses based only on the second audio data.

9. The method of claim 8, further comprising:
   detecting one or more signal attributes of the second audio data that also occur in the first audio data; and
   timing the delivery of the second sequence of stimulation pulses to the second ear of the recipient based on a timing of the one or more signal attributes in the second audio data,
   wherein the first device is configured to time delivery of the first sequence of stimulation pulses based on a timing of the one or more signal attributes in the first audio data.

10. A system, comprising:
    a first device configured to:
      receive a first set of sound signals generated by at least one sound source,
      convert the first set of sound signals into a first stimulation pulse train, wherein the first stimulation pulse train is artificially amplitude modulated based on a fundamental frequency associated with the at least one sound source, and
      deliver the first stimulation pulse train to a first ear of a recipient of the system; and
    a second device configured to:
      receive a second set of sound signals generated by the at least one sound source,
      convert the second set of sound signals into a second stimulation pulse train, wherein the second stimulation pulse train is artificially amplitude modulated based on the fundamental frequency associated with the at least one sound source, determine, relative to delivery of the first stimulation pulse train to the first ear of the recipient, a time delay for delivery of the second stimulation pulse train to a second ear of the recipient, and deliver the second stimulation pulse train to the second ear of the recipient at a time corresponding to the time delay.

11. The system of claim 10, wherein to determine the time delay for delivery of the second stimulation pulse train to a second ear of the recipient, the second device is configured to:

determine the time delay from an Interaural Time Difference (ITD) associated with receipt of the first set of sound signals at the first device and receipt of the second set of sound signals at the second device.

12. The system of claim 11, wherein the time delay for delivery of the second stimulation pulse train relative to the delivery of the first stimulation pulse train is substantially equal to the ITD.

13. The system of claim 11, wherein the time delay for delivery of the second stimulation pulse train relative to the delivery of the first stimulation pulse train is greater than the ITD.

14. The system of claim 10:

wherein the first device is configured to send first audio data to the second device, wherein the first audio data is generated from the first set of sound signals; and wherein the second device is configured to send second audio data to the first device, wherein the second audio data is generated the second set of sound signals.

15. The system of claim 14, wherein the second device is configured to determine the time delay for delivery of the second stimulation pulse train relative to the delivery of the first stimulation pulse train based on the second set of sound signals and the first audio data.

16. Non-transitory computer readable storage media encoded with instructions that, when executed by one or more processors, cause the one or more processors to:

generate, at a first device, a first sequence of stimulation pulses representative of first audio data received at the first device;

generate, at a second device, a second sequence of stimulation pulses representative of second audio data received at the second device;

modulate the first sequence of stimulation pulses based on one or more features of the first audio data and the second audio data;

modulate the second sequence of stimulation pulses based on the one or more features of the first audio data and the second audio data; and synchronize a timing of delivery of the first sequence of stimulation pulses to a first ear of a recipient with a timing of delivery of the second sequence of stimulation pulses to a second ear of the recipient.

17. The non-transitory computer readable storage media of 16, wherein the one or more features of the first audio data and the second audio data comprise a frequency of the first audio data and the second audio data.

18. The non-transitory computer readable storage media of claim 17, wherein the frequency is a fundamental frequency related to one or more sound sources in an audio environment, and wherein the instructions to synchronize the timing of delivery of the first sequence of stimulation pulses with the timing of delivery of the second sequence of stimulation pulses comprise instructions that, when executed by the one or more processors, cause the one or more processors to:

synchronize the timing of the delivery of the first sequence of stimulation pulses to a first ear of a recipient with the timing of delivery of the second sequence of stimulation pulses to a second ear of the recipient based on a relative location of the one or more sound sources in the audio environment.

19. The non-transitory computer readable storage media of claim 16, wherein the instructions to synchronize the timing of delivery of the first sequence of stimulation pulses with the timing of delivery of the second sequence of stimulation pulses comprise instructions that, when executed by the one or more processors, cause the one or more processors to:

synchronize the timing of the delivery of the first sequence of stimulation pulses and the second sequence of stimulation pulses based on one or more signal attributes occurring in both of the first audio data and the second audio data.

20. The non-transitory computer readable storage media of claim 19, wherein the one or more signal attributes occur in the first audio data and the second audio data with a relative timing corresponding to an Interaural Time Difference (ITD) associated with receipt of the first audio data at the first device and receipt of the second audio data at the second device.

* * * * *